United States Patent [19]
Grunwell et al.

[11] 4,087,524
[45] May 2, 1978

[54] ANDROST-4-EN-19-OLS FOR THE ENHANCEMENT OF LIBIDO

[75] Inventors: Joyce F. Grunwell, Hamilton, Ohio; Vladimir Petrow, Chapel Hill, N.C.

[73] Assignee: Richardson-Merrell Inc., Wilton, Conn.

[21] Appl. No.: 766,238

[22] Filed: Feb. 7, 1977

Related U.S. Application Data

[63] Continuation-in-part of Ser. No. 461,011, Apr. 15, 1974, which is a continuation-in-part of Ser. No. 329,849, Feb. 5, 1973, abandoned.

[51] Int. Cl.$^2$ ............................................. A61K 31/56
[52] U.S. Cl. .................... 424/238; 424/241; 424/242; 424/243
[58] Field of Search ............... 424/238, 241, 242, 243

[56] References Cited

U.S. PATENT DOCUMENTS

| 2,819,276 | 1/1958 | Mihina | 260/397.4 |
| 3,278,528 | 10/1966 | Bowers et al. | 260/397.4 |

OTHER PUBLICATIONS

Applezweig, "Steroid Drugs," McGraw-Hill Book Co. Inc. New York, (1962) p. 273.

Primary Examiner—Elbert L. Roberts
Attorney, Agent, or Firm—William J. Stein; Eugene O. Retter

[57] ABSTRACT

Derivatives of androst-4-en-19-ol are described which are useful in enhancing the libido and related psychic attitudes in primates.

5 Claims, No Drawings

ANDROST-4-EN-19-OLS FOR THE ENHANCEMENT OF LIBIDO

CROSS REFERENCE TO RELATED APPLICATIONS

This application is a continuation-in-part of U.S. application Ser. No. 461,011, filed Apr. 15, 1974, which is a continuation-in-part of application Ser. No. 329,849, filed Feb. 5, 1973, now abandoned.

DESCRIPTION OF THE PRIOR ART

U.S. Pat. No. 2,819,276 discloses 3,19-dihydroxy-4-androsten-17-one useful for its estrogenic properties. Additionally, the reference discloses the corresponding 3-ketones. The 3,19-dihydroxy steroids are stated to be useful as intermediates for the preparation of 19-hydroxy and 19-norsteroids. The 19-norsteroids are stated to possess anabolic and hypotensive action. The most closely related novel compounds of this invention differ from the prior art in possessing an additional ether group in either the 3,17 and/or 19-positions. In addition the compounds of the present invention possess a totally different and surprising utility from that which is disclosed in the prior art.

U.S. Pat. No. 3,278,528 discloses the preparation of 5α-halo-4β,19-oxido androstanes, pregnanes and spirostanes. The reference teaches the conversion of these compounds to certain 3,17-substituted-androst-4-en-19-ols and 3,17,19-substituted androst-4-enes which are closely related to the novel compounds of this invention. The prior art compounds are stated to be useful as anabolic-androgenic agents having a favorable anabolic-androgenic ratio. Additionally they are stated to have "anti-estrogenic, anti-gonadotrophic, anti-fibrillatory and appetite stimulating properties . . . lower the blood cholesterol level, relieve premenstrual tension and suppress the output of the pituitary gland." However, the most closely related novel compounds of this invention all differ in that one or more of the 3,17 and-/or 19-positions must be etherified. Furthermore the novel compounds described herein possess the remarkable ability of enhancing the libido of primates, a utility not previously described nor associated with the class of androst-4-en-19-ols and its derivatives.

Rao and Axelrod, J. Org. Chem, 27, 4694-6 (1962) describe the preparation of the 17-tetrahydropyranyl ethers of 19-hydroxy-androst-4-en-3-one and 19-acetoxy-androst-4-en-3-one, respectively. The reference teaches their usefulness as intermediates in the synthesis of 17β-hydroxy-androst-4-ene-3,19-dione. However, no indication of the utility for these compounds is given other than as chemical intermediates in the reference.

Hormones are generally recognized as being of significance in the biochemical regulation of the psyche and sexual behavior, Hubble, Lancet, Aug. 3, 1963, 209-214. The aromatization and conversion of diverse androgens to estrogen is reported to be responsible for the induction of estrous behavior in the female of certain non-primate species such as the rabbit, Beyer et al., Endocrinology, 87, 1386-1389 (1970). It is also known that estrogen does not form the endocrinological basis for sexual drive in either the male or the female primate, Everitt et al., Physiology and Behavior 8, 409-415 (1972). Accordingly, it would appear that androgens which are capable of aromatization to estrogen would be ineffective in the primate.

In contradistinction thereto, applicants have surprisingly discovered a useful class of androst-4-en-19-ols, comprising both new and some previously reported compounds, which is capable of being aromatized to estrogen. These compounds are highly effective in enhancing the libido of both male and female primates, as well as in improving related psychic attitudes associated therewith. Furthermore, these compounds can be used without obtaining any concomitant, overt, androgenic, somatic side-effects, a result not previously achieved.

SUMMARY OF THE INVENTION

This invention relates to the unexpected and surprising discovery that certain novel compounds, in addition to certain compounds which have been described in the prior art, possess the property of enhancing a diminished libido as well as enhancing related psychic attitudes in man and other primates without demonstrating any overt androgenic or estrogenic response upon the secondary sex structures. More particularly, the class of compounds which possess this novel utility is represented by the general formula:

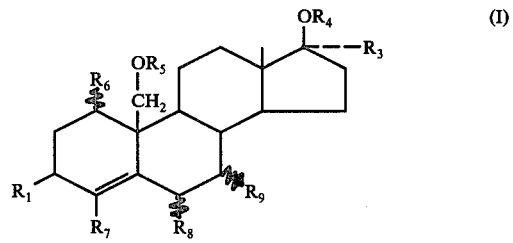

wherein
- $R_1$ is selected from the group consisting of $H_2$, oxo and $H(OR_2)$,
- $R_2$, $R_4$ and $R_5$ are each selected from the group consisting of hydrogen, acyl having from 1 to 12 carbon atoms, lower alkyl having from 1 to 3 carbon atoms, trialkylsilyl in which the alkyl group has from 1 to 5 carbon atoms, triphenylsilyl, 2-tetrahydropyranyl, 4-tetrahydropyranyl, 1-cycloalkenyl having from 5 to 7 carbon atoms, 1-methoxycycloalkyl and 1-ethoxycycloalkyl in which the cycloalkyl group has from 5 to 7 carbon atoms,
- $R_3$ is selected from the group consisting of hydrogen, lower alkyl having from 1 to 6 carbon atoms, lower alkenyl having from 2 to 6 carbon atoms, and lower alkynyl having from 2 to 6 carbon atoms, and $R_3$ and $OR_4$ when taken together is oxo,
- $R_6$, $R_7$ $R_8$ and $R_9$ are hydrogen and methyl.

DETAILED DESCRIPTION OF THE INVENTION

As shown in formula (I) above, the compounds of the present invention are substituted in the 1, 3, 4, 6, 7, 17 and 19-positions of the androst-4-ene nucleus.

The symbol $R_1$ represents various substituents located at the 3-position of the nucleus. Suitable substituents include two hydrogen atoms, an oxo group, and either a substituted or an unsubstituted hydroxyl group. The substituted or unsubstituted hydroxyl group, represented by the symbol $H(OR_2)$, can be present in either its alpha or beta configuration. When the symbol $R_2$ represents hydrogen, the free alcohol is, of course, delineated. When the symbol $R_2$ represents acyl, an ester is present at the 3-position. Finally, when $R_2$ represents lower alkyl having from 1 to 3 carbon atoms, trialkylsilyl in which the alkyl group has from 1 to 5 carbon atoms, triphenylsilyl, 2-tetrahydropyranyl, 4-tetrahydropyranyl, 1-cycloalkenyl having from 5 to 7 carbon atoms, 1-methoxycycloalkyl and 1-ethoxycycloalkyl in which the cycloalkyl group has from 5 to 7 carbon atoms, the 3-ethers are delineated.

The acyl esters present in the 3-position are derived from monobasic alkyl or aralkyl carboxylic acids having from 1 to 12 carbon atoms. The carboxylic acids from which these acylates are derived include saturated and unsaturated aliphatic acids as well as aromatic acids, as for example, acetic, propionic, butyric, isobutyric, valeric, isovaleric, caproic, caprylic, decanoic, dodecanoic, acrylic, crotonic, cyclobutanecarboxylic, cyclopentanecarboxylic, cyclopentenecarboxylic, cyclohexanecarboxylic, benzoic, toluic, naphthoic, ethylbenzoic, phenylacetic, naphthaleneacetic, phenylvaleric, cinnamic, phenylpropionic, p-propyloxyphenylpropionic and p-butyloxyphenylacetic acid.

The term lower alkyl as used with regard to the ether substitution in the 3-position refers to groups having from 1 to 3 carbon atoms, as for example, methyl, ethyl, propyl and isopropyl. Silyl ethers containing a tetrasubstituted silicon atom are similarly substituted with three lower alkyl groups having from 1 to 5 carbon atoms. Alternatively, the silicon atom can be substituted with three phenyl radicals. Ethers which are present in the 3-position also include unsaturated cycloalkane ethers having from 5 to 7 carbon atoms in which the unsaturation is present in a position alpha to the ether oxygen as represented by the term 1-cycloalkenyl. Illustrative of such groups are the 1-cyclopentenyl, 1-cyclohexenyl or 1-cycloheptenyl radicals. The corresponding saturated cycloalkane ethers are also considered to be within the scope of this invention but here the cycloalkane group is further substituted with a methoxy or an ethoxy radical at its point of attachment, i.e., at the 1-position of the cycloalkyl ring. Typical of the saturated heterocyclic radicals which are present as ethers in the 3-position are the 2-tetrahydropyranyl and the 4-tetrahydropyranyl radicals.

The symbols $R_2$, $R_4$ and $R_5$ all represent identical sets of substituents at the 3, 17$\beta$ and 19-positions of the androst-4-ene nucleus, respectively. Each can be varied independently of one another. Suitable substituents include hydrogen to indicate that they may be mono, di or tri-substituted hydroxyl groups. Additional substituents include an acyl ester or a lower alkyl, silyl, tetrahydropyranyl, saturated or unsaturated cycloalkyl ether as previously defined in the 3-position above.

The symbol $R_3$ represents the 17$\alpha$-position and can be either a hydrogen atom or a saturated or unsaturated aliphatic chain having from 1 to 6 carbon atoms. Illustrative of such groups are straight or branched chain alkyl radicals, as for example, methyl, ethyl, propyl, isopropyl, butyl, sec-butyl, isoamyl, n-pentyl and n-hexyl. Illustrative of the alkenyl groups which can be present are the vinyl, allyl, 1-butenyl, 1-pentenyl and 1-hexenyl radicals. Illustrative of the alkynyl groups which may be present are the ethynyl, 1-propynyl and 1-butynyl radicals. It should be noted that the symbols $R_3$ and $OR_4$ when taken together can also represent an oxo radical, thereby forming a class of 19-(substituted)-hydroxy-androst-4-en-17-ones. The remaining symbols $R_6$, $R_7$, $R_8$ and $R_9$ each represent hydrogen or methyl.

A preferred class of compounds within the scope of the present invention includes the 17$\beta$,19-dihydroxy-androst-4-en-3-ones and the 19-ethers and esters thereof. This class of compounds is delineated when the symbol $R_1$ is oxo and the symbol $R_4$ is hydrogen. Illustrative of the species within this preferred class are the compounds:

17$\beta$,19-dihydroxy-androst-4-en-3-one,
17$\beta$-hydroxy-19-trimethylsiloxy-androst-4-en-3-one,
17$\beta$-hydroxy-19-triphenylsiloxy-androst-4-en-3-one,
17$\beta$-hydroxy-19-(4'-tetrahydropyranyloxy)androst-4-en-3-one,
19-(1'-cyclopentenyloxy)-17$\beta$-hydroxy-androst-4-en-3-one,
17$\beta$-hydroxy-19-propoxy-androst-4-en-3-one,
19-tributylsiloxy-17$\beta$-hydroxy-androst-4-en-3-one,
17$\alpha$-ethynyl-17$\beta$,19-dihydroxy-androst-4-en-3-one 19 acetate,
19-(2'-tetrahydropyranyloxy)-17$\beta$-hydroxy-17$\alpha$-propyl-androst-4-en-3-one,
17$\alpha$-(1-butynyl)-17$\beta$,19-dihydroxy-androst-4-en-3-one 19-dodecanoate,
17$\beta$-hydroxy-19-triethylsilyloxy-4$\beta$-methyl-androst-4-en-3-one,
17$\beta$,19-dihydroxy-7$\alpha$-methyl-androst-4-en-3-one 19-propionate, and
17$\alpha$-ethyl-17$\beta$-hydroxy-19-(1'-methoxycycloheptyloxy)androst-4-en-3-one.

A second preferred class of compounds within the scope of the present invention includes the 19-hydroxy-androst-4-ene-3,17-diones and the ethers and esters thereof. This class of compounds is delineated when the symbol $R_1$ is oxo and the symbols $R_3$ and $OR_4$ when take together are oxo. Illustrative of the species within this preferred class are the compounds:

19-hydroxy-androst-4-ene-3,17-dione,
19-trimethylsiloxy-androst-4-ene-3,17-dione,
19-triphenylsiloxy-androst-4-ene-3,17-dione,
19-hydroxy-4$\beta$-methyl-androst-4-ene-3,17-dione 19-propionate,
19-(1'-methoxycycloheptyloxy)-7$\alpha$-methyl-androst-4-ene-3,17-dione,
6$\beta$-methyl-19-triethylsiloxy-androst-4-ene-3,17-dione,
19-hydroxy-androst-4-ene-3,17-dione 19-dodecanoate,
19-(2'-tetrahydropyranyloxy)androst-4-ene-3,17-dione,
19-hydroxy-androst-4-ene-3,17-dione 19-acetate,
19-tributylsiloxy-4$\beta$-methyl-androst-4-ene-3,17-dione,
19-propoxy-androst-4-ene-3,17-dione,
19-(1'-cyclopentenyloxy)-4$\beta$,6$\alpha$-dimethyl-androst-4-ene-3,17-dione, and
19-(4'-tetrahydropyranyloxy)androst-4-ene-3,17-dione.

The novel alkyl ethers are prepared from their corresponding hydroxy steroids by reaction with an alkylating agent such as trimethyloxonium fluoroborate, triethyloxonium fluoroborate or methylfluorosulfonate in an inert chlorocarbon solvent such as methylene chloride. Alternatively, alkylating agents such as alkyl halides, alkyl tosylates, alkyl mesylates and dialkylsulfate may be used with a base such as silver oxide or barium oxide in polar, aprotic solvents as for example, dimethylformamide, dimethyl sulfoxide and hexamethylphosphoramide. The hydroxyl groups can be silylated by reaction with silylating agents such as trialkylchlorosilane, triarylchlorosilane, N-trialkylsilylacetamide in the presence of an amine base such as triethylamine or pyridine to prepare the novel silyl ethers.

The 2-tetrahydropyranyl ethers are prepared from the corresponding hydroxy steroids by reaction with dihydropyran in the presence of an acid catalyst, as for example, hydrochloric acid, p-toluenesulfonic acid or phosphorous oxychloride.

The 4-tetrahydropyranyl ethers are prepared by reacting the hydroxy steroid, 4-bromotetrahydropyran and a base such as sodium hydride together in a polar aprotic solvent such as dimethylformamide, dimethylsulfoxide or hexamethylphosphoramide.

The 1-alkoxycycloalkoxy derivatives are prepared by reacting the hydroxy steroids with a loweralkylketal of a cycloalkanone or the lower alkylenol ether of a cycloalkanone or mixture of these reagents in the presence of an acidic catalyst such as p-toluenesulfonic acid, pyridine hydrochloride, pyridine p-toluenesulfonate. The reaction is generally conducted in a solvent such as dioxane, methylene chloride, ether or t-butanol at a temperature less than 70° C., and preferably at 25° C. The preparation of suitable cycloalkyl derivatives is achieved using such reagents as cyclopentanone diethylketal, cyclohexanone dimethylketal, 1-methoxy-1-cyclopentene or 1-ethoxy-1-cyclohexane. Following essentially the same procedure, the 1-cycloalkenyl ethers are prepared directly using, however, higher boiling solvents so that the reaction temperature is above 70° C. Suitable solvents include benzene, toluene and dimethylformamide. Alternatively, the 1-cycloalkenylethers can be prepared via a pyrolysis of the isolated 1-alkoxycycloalkoxysteroid in the presence of a trace of an organic base such as pyridine utilizing a high boiling solvent such as benzene or dimethylformamide.

The 3-deoxy-19-substituted androstanes are readily prepared by conversion of the 3-ketone to the 3-ethylenethioketal, followed by Raney nickel desulfurization. Thus, 7α-methyl-4-androsten-17β,19-diol and 6α-methyl-4-androsten-17β,19-diol dipropionate are readily prepared in this manner from 17β,19-dihydroxy-7α-methyl-4-androsten-3-one and 17β,19-dihydroxy-6α-methyl-4-androsten-3-one dipropionate, respectively.

Reduction of the androst-4-en-3-ones with metal hydrides such as lithium aluminum hydride, lithium tri-t-butoxyaluminum hydride and sodium borohydride produces the corresponding 3β-alcohol. The use of a highly hindered lithium or potassium trialkylborohydride such as potassium tri-sec-butylborohydride results in the formation of the axial alcohol, namely, the androst-4-en-3α-ol.

The reaction of dichlorodicyanobenzoquinone with 19-hydroxy-4-androsten-3-ones in refluxing dioxane or methylenechloride for 24–72 hours produces the corresponding 19-hydroxy-1,4-androstadien-3-one. However, two restrictions in this sequence are necessary. First, the 19-hydroxy group must be protected as an ester or ether in order to avoid aromatization. Secondly, the 1-position must possess an axial hydrogen atom for elimination. Thus, the 1α-methyl androstene is not reactive although the 1β-methyl androstane is. Following this procedure 17β,19-dihydroxy-7α-methyl-4-androsten-3-one dipropionate is converted to 17β,19-dihydroxy-7α-methyl-1,4-androstadien-3-one dipropionate. Similarly, 19-hydroxy-6α-methyl-4-androsten-3,17-dione acetate forms 19-hydroxy-6α-methyl-1,4-androstadien-3,17-dione acetate and 1β-methyl-19-tetrahydropyranyloxy-4-androsten-3,17-dione forms 1-methyl-19-tetrahydropyranyloxy-1,4-androstadien-3,17-dione.

The 1α-methyl-19-substituted-androst-4-enes are produced by reacting the corresponding androsta-1,4-dien-3-ones with dimethyllithium copper. Methylation is preferably conducted by adding the androsta-1,4-dien-3-one dissolved in an inert solvent, to a solution of dimethyllithium copper in the same or a different inert solvent. Suitable inert reaction solvents include methylene chloride, tetrahydrofuran, dioxane, hexane, benzene with diethyl ether being the solvent preferred. The reaction is conducted at temperatures between −75° C. and 20° C. with a temperature range of from about −5° C. to 0° C. being preferred. The ratio of reactants is not critical, but at least 2 molar equivalents of dimethyllithium copper must be present for each conjugate addition. The presence of free hydroxyl groups will, of course, require additional equivalent amounts of the organometallic reagent. Following this procedure, 19-hydroxy-androst-1,4-diene-3,17-dione propionate can be converted to 19-hydroxy-1α-methyl-androst-4-en-3,17-dione propionate.

The 1β-methyl-19-substituted-4-androst-3-ones are synthesized in the manner of Simmons and Smith by treatment of a 19-substituted-androsta-1,5-diene-3β-ol with methylenediiodide and a zinc-copper couple to form the 19-substituted-1β,2β-methylene-androst-5-ene-3β-ol. The presence of the 3β-alcohol as well as the 19-alcohol direct the insertion to the beta side. The 1β,2β-methylene-3β-ol is then oxidized to a 3-one and the cyclopropyl ring cleaved by acid or base to form the 19-substituted-1β-methyl-4-androsten-3-one. Typically a mixture of zinc-copper couple, iodine and methylenediiodide in an inert solvent such as diethylether, tetrahydrofuran, dioxane or diglyme is heated with an infrared lamp for thirty minutes. The steroid, also is an inert solvent as above, is added and the mixture heated from 25° to 100° for 30 minutes to 72 hours. Generally, reflux temperatures of the solvent employed combined with a 24 hour reflux period is sufficient. The Simmons-Smith reagent is taken in 5–10 fold excess. The oxidation of the 3-alcohol is readily achieved with various oxidizing agents. Illustrative oxidizing agents are Jones reagent, CrO₃.pyridine complex (Sarett reagent), and Cornforth reagent. However, if the 19-alcohol is not suitably protected, it also will be oxidized. The remaining 1β,2β-methylene ring is then cleaved to the 1β-methyl group by refluxing with zinc in acetic acid. In this manner 19-tetrahydropyranyloxy-1,5-androstadien-3,17-diol is converted to 1β-methyl-19-hydroxy-4-androstene-3,17-dione.

Methylation of 19-hydroxy-4-androsten-3-ones using Atwater's procedure (N. W. Atwater, J. Am. Chem. Soc. 79, 5315 (1957)) of adding methylchloride slowly to a refluxing solution of the ketone in t-butanol containing only a small excess of potassium t-butoxide produces the 19-hydroxy-4-methyl-4-androsten-3-ones in fair yield. Following this procedure 19-hydroxy-7α-methyl-androst-4-ene-3,17-dione and 17β,19-hydroxy-1α,7α-dimethyl-androst-4-en-3-one can be converted to 19-hydroxy-4,7α-dimethyl-androst-4-ene-3,17-dione and 17β,19-dihydroxy-1α,4,7α-trimethylandrost-4-en-3-one, respectively.

Alternatively, the 19-hydroxy-4-androsten-3-one can be selectively thiomethylated at position 4 with formaldehyde and a thiol under basic conditions. Benzylmercaptan is the preferred thiol. Desulphurisation of the intermediate 19-hydroxy-4-phenylthiomethyl-4-androsten-3-one leads to the monomethylated 19-hydroxy-4-methyl-4-androsten-3-one in good yield.

Treatment of 5α,6α-epoxyandrostane-3,19-diol or a 3,3-ethylenedioxy-5α,6α-epoxyandrostan-19-ol with methylmagnesium bromide in dry solvents such as diethyl ether, tetrahydrofuran, benzene or toluene at temperatures between 0° C. to 100° C., results in epoxide cleavage to give the corresponding 6β-methyl-androstane-5α,19-diols. The corresponding 3-alcohol can be oxidized or the ketal group hydrolysed with hot acetic acid or dilute aqueous methanolic mineral acid to form the 5α-hydroxy-6β-methyl-3-ketone. Dehydration of the β-hydroxy ketone with sodium hydroxide in hot aqueous methanol is accompanied by inversion at 6 to form the 6α-methylandrost-4-en-3-one. In this manner the compounds 17β,19-dihydroxy-6α-methyl-4-androsten-3-one, 17β-hydroxy-6α,17α-dimethyl-4-androstene-3,19-dione are prepared starting with 3,3-ethylenedioxy-5α,6α-epoxyandrostan-17,19-diol and 5α,6α-epoxy-17α-methylandrostan-3β,17β,19-diol, respectively.

The 7α-methyl-4-androstene-3,19-diones are produced by alkylating the corresponding 4,6-androstadiene-3,19-dione with dimethyllithium copper in an inert solvent such as diethyl ether, tetrahydrofuran, hexane or mixtures of these at temperatures ranging from −78° C. to 25° C. Tetrahydrofuran is the preferred solvent and temperatures between −5° C. to 10° C. provide optimum results. Quenching the initially formed enolate anion with a weak protonating agent such as a saturated solution of ammonium chloride, oxalic acid or boric acid provides the 7α-methyl-5-androstene-3,19-dione. Quenching the enolate with a strong protonating agent such as hydrochloric acid provides the 7α-methyl-4-androstene-3,19-diones.

The 7α-methyl-4-androstene-3,19-dione can also be prepared by either acid or base catalyzed isomerization of the corresponding 7α-methyl-5-androstene-3,19-dione. Suitable acid catalysts include hydrochloric acid, sulfuric acid, p-toluenesulfonic acid and acetic acid and they can be used in such solvents as methanol, ethanol, dioxane, tetrahydrofuran and methylenechloride. Suitable base catalysts for this isomerization include sodium hydroxide or sodium methoxide in an alcohol solvent such as methanol.

Following this procedure 1α,7α-dimethyl-4-androstene-3,17,19-trione, 7α-methyl-17β-(2'-tetrahydropyranyloxy)-4-androstene-3,19-dione and 17β-hydroxy-7α,17α-dimethyl-4-androstene-3,19-dione are prepared starting with 1α-methyl-4,6-androstadiene-3,17,19-trione, 17β-(2'-tetrahydropyranyloxy)-4,6-androstadiene-3,19-dione and 17β-hydroxy-4,6-androstadiene-3,19-dione. These 7α-methyl-4-androstene-3,19-diones can be reduced to the diols with reagents such as lithium aluminum hydride, lithium tri-t-butoxyaluminumhydride, sodium borohydride or potassium borohydride. The 3-hydroxyl group can then be selectively oxidized with reagents specific for allylic alcohol oxidation such as activated manganese dioxide or dichlorodicyanobenzoquinone. Following this procedure the 19-hydroxy-4-androsten-3-one is prepared. More specifically, 1α,7α-dimethyl-4-androstene-3,17,19-trione can be converted to 1α,7α-dimethyl-4-androstene-3β,17β,19-triol and 17β,19-dihydroxy-1α,7α-dimethyl-4-androsten-3-one. Similarly, 7α-methyl-17β-(2'-tetrahydropyranyloxy)-4-androstene-3,19-dione can be converted to 7α-methyl-17β-(2'-tetrahydropyranyloxy)-4-androstene-3β,19-diol and 19-hydroxy-7α-methyl-17β-(2'-tetrahydropyranyloxy)-4-androsten-3-one. p The 19-hydroxy-androst-4-en-3-ones used in the present invention are, broadly speaking, prepared by the methods described in Vol. II of Organic Reactions in Steroid Chemistry, Edited by J. Fried and J. A. Edwards, p. 237–87; van Nostrand Reinhold Company, N.Y., (1972). One route to the 19-hydroxyandrost-4-en-3-ones proceeds from the 5α-halogen-6β,19-ether intermediates. These compounds are prepared from the corresponding 5,6-unsaturated steroids by the addition of a hypohalous acid forming the 5α-halogen-6β-carbinols, which are subsequently cyclized by means of lead tetraacetate or by decomposition of the 6β-hypohalites to yield the desired 5α-halogen-6β,19-ethers. Thus, for example, 3β,17β-dihydroxy-5-androstene diacetate is converted to 5α-bromo-3β,6β,17β-trihydroxyandrostane 3,17-diacetate by means of hypobromous acid. Lead tetraacetate or hypoiodide converts this to 5α-bromo-3β,17β-dihydroxy-6β,19-oxidoandrostane 3,17-diacetate. Likewise, 3β-hydroxyandrost-5-en-17-one acetate is converted to 5α-chloro-3β,6β-dihydroxyandrostan-17-one 3-acetate by means of hypochlorous acid. A lead tetraacetate or hypoiodite oxidation converts this latter compound into 5α-chloro-3β-hydroxy-6β,19-oxidoandrostane-17-one acetate. This 17-ketone reacts with an organometallic reagent such as methylmagnesium bromide or lithium acetylide to form the desired 17α-alkylated 17β-hydroxy derivative.

The 3-oxo-4-ene group is next introduced by oxidizing the 3β-hydroxy-5α-halo-6β,19-oxido intermediate with an oxidizing reagent such as chromium trioxide. Subsequent dehydrohalogenation using pyridine or sodium acetate in methanol results in the formation of the corresponding 6β,19-oxidoandrost-4-en-3-one. This 6β,19-ether is reductively cleaved using reagents such as zinc and isopropanol, zinc and acetic acid or lithium and ammonia to form the desired 19-hydroxyandrost-4-en-3-one. In addition to providing the 19-hydroxyandrostane starting materials for either introduction of methyl groups at 1,4,6,7 either singly or in combinations, this reaction sequence can be carried out with the methyl groups in these positions already present to produce the compounds of this invention directly.

An alternative route to the 19-hydroxyandrost-4-en-3-ones proceeds from the 6β,19-oxido-3α,5α-cycloandrostanes as intermediates. These compounds are in turn prepared by a lead tetraacetate or hypoiodite oxidation upon the corresponding 6β-hydroxy-3α,5αcycloandrostane, an i-steroid. Heating the 6β,19-ether in a solvent such as dimethylsulfoxide with benzoylperoxide results in cleavage and the direct formation of the 19-hydroxyandrost-4-en-3-one. Alternatively, the 6β,19 ether can be cleaved to the corresponding 3β,19-dihydroxy-5-androstene using sulfuric acid in an aqueous acetone solution. This compound is then oxidized to the desired 19-hydroxyandrost-4-en-3-one by means of an Oppenauer oxidation.

The novel 3,17 and 19 ethers of this invention are selectively prepared by protection of the hydroxy groups, by selective oxidation or selective reduction sequences. The compound 19-hydroxy-androst-4-ene-3,17-dione is etherified in the manner previously described to produce the 19-OR$_1$ derivatives of androst-4-ene-3,17-dione. Reduction of these ketones with lithium aluminum hydride, lithium trialkoxyaluminum hydride or sodium borohydride results in the formation of the corresponding 3,17-dihydroxy analogues. Thus, for example, 19-trimethylsiloxyandrost-4-ene-3,17-dione, 19-tetrahydropyranyloxyandrost-4-ene-3,17-dione, 19-methoxyandrost-4-ene-3,17-dione are converted by the above procedure to 19-trimethylsiloxyandrost-4-en-3$\beta$,17$\beta$-diol, 19-tetrahydropyranyloxyandrost-4-ene-3$\beta$,17$\beta$-diol and 19-methoxyandrost-4-en-3$\beta$,17$\beta$-diol respectively.

The compound 17$\beta$,19-dihydroxyandrost-4-en-3-one is similarly etherified to form the 17$\beta$-OR$_4$, 19-OR$_1$, derivatives of androst-4-en-3-one. Reduction as previously described yields the corresponding 3-hydroxy analogues. For example, 17$\beta$,19-dihydroxyandrost-4-en-3-one is converted to 17$\beta$,19-di-triphenylsiloxyandrost-4-en-3-one and 17$\beta$,19-di-(1-methoxy-1-cyclopentyloxy)-androst-4-en-3-one as previously described. These compounds are then reduced using lithium aluminum hydride in an ether or tetrahydrofuran solution to produce 17$\beta$,19-di-triphenylsiloxyandrost-4-en-3$\beta$-ol and 17$\beta$,19-di-(1-methoxy-1-cyclopentyloxy)-androst-4-en-3$\beta$-ol, respectively.

The 3,17,19-triethers are readily available from androst-4-ene-3$\beta$,17$\beta$,19-triol in the manner presented earlier. The 3,17-diethers are also available. For example, 19-hydroxyandrost-4-ene-3,17-dione is acetylated in the usual manner with acetic anhydride and pyridine to form the corresponding 19-acetate. The 3,17-diketones are then selectively reduced using lithium tri-t-butoxy aluminum hydride to give androst-4-ene-3$\beta$,17$\beta$,19-triol 19-acetate. Etherification of positions 3 and 17 in the aforementioned manner results in the preparation, for example, of 3$\beta$,17$\beta$-(1-cyclopentenyloxy)-androst-4-en-19-ol acetate or 3$\beta$,17$\beta$-ditetrahydropyranyloxyandrost-4-en-19-ol acetate. Cleavage of these 19-acetates with lithium aluminum hydride results in the formation of 3$\beta$,17$\beta$-(1-cyclopentenyloxy)-androst-4-en-19-ol and 3$\beta$,17$\beta$-ditetrahydropyranyloxyandrost-4-en-19-ol, respectively.

Acyl groups are introduced by standard methods known to those skilled in the art such as the reaction with an acid anhydride or chloride in the presence of an alkaline component such as pyridine. Mixed ether/esters are prepared by suitable combinations of these general methods. For example, 17$\beta$,19-dihydroxyandrost-4-en-3-one can be acetylated to form the diacetate. The remaining 3-ketone is reduced to the corresponding alcohol and etherified to yield a 3-ether-17,19-diacetate. Cleavage of the 17,19-diacetate to the corresponding alcohols as previously described results in the preparation, for example, of 3$\beta$-methoxy-androst-4-ene-17$\beta$,19-diol and 3$\beta$-(1-ethoxycyclohexyloxy)-androst-4-ene-17$\beta$,19-diol, respectively.

A 17$\beta$,19-dihydroxy-4-androsten-3-one diester can be selectively hydrolyzed to the 17-monoester by refluxing one hour in 10% aqueous methanol containing one equivalent sodium bicarbonate. In this manner 17$\beta$,19-dihydroxy-4-methyl-4-androsten-3-one dipropionate and 17$\beta$,19-dihydroxy-4-androsten-3-one diacetate are converted to 17$\beta$,19-dihydroxy-4-methyl-4-androsten-3-one 17-propionate and 17$\beta$,19-dihydroxy-4-androsten-3-one 17-acetate, respectively.

A 19-hydroxy-4-androstene-3,17-dione can be selectively reduced to 17$\beta$,19-dihydroxy-4-androsten-3-one by the action of potassium borohydride in ethanol at −10° to 0° C. for reaction periods of less than 5 hours. In this manner 6$\alpha$-methyl-19-(2'-tetrahydropyranyloxy)-4-androstene-3,17-dione and 19-ethoxy-1$\alpha$-methyl-4-androstene-3,17-dione can be selectively reduced to 17$\beta$-hydroxy-6$\alpha$-methyl-19-(2'-tetrahydropyranyloxy)-4-androsten-3-one and 19-ethoxy-17$\beta$-hydroxy-1$\alpha$-methyl-4-androsten-3-one, respectively.

A 4-androstene-3$\beta$,17$\beta$,19-triol can be selectively oxidized to a 17$\beta$,19-dihydroxy-4-androsten-3-one by activated manganese dioxide in an inert solvent such as methylene chloride or chloroform at temperatures below 25° C. Elevated temperatures promote oxidation at position 19. This selective allylic oxidation is also accomplished by the action of dichlorocyanobenzoquinone on the triol in solvents such as dioxane or methylenechloride. The preferred temperature is below 25° C. and typical reaction times range from about 1 to about 18 hours. With these reagents 1$\beta$-methyl-4-androstene-3$\beta$,17$\beta$,19-triol and 17$\alpha$-ethinyl-4-androstene-3$\beta$,17$\beta$,19-triol are converted to 17$\beta$,19-dihydroxy-1$\beta$-methyl-4-androsten-3-one and 17$\alpha$-ethinyl-17$\beta$,19-dihydroxy-4-androsten-3-one, respectively.

The compounds of this invention, represented by formula (I), are useful in modulating the behavior of normal, non-hostile animals when placed in contact with hostile aggressive animals. Hostile aggression in animals can be induced by prolonged isolation of individual animals in the dark. Modulation of the behavioral response in the treated, normally non-hostile animals towards the aggressive animals broadly suggests their use in humans for certain psychasthenic syndromes and related conditions of mental health.

Applicants have made the further important discovery that the 19-hydroxy-androst-4-enes described in formula (I) above, possess the remarkable ability of enhancing libido and related psychic attitudes in man and other primates. The expression "libido" as used herein refers, in general, to the sexual interest and sexual drive of mammals. However, as used herein, the expression "libido" is also intended to include certain psychic attitudes in primates, particularly man, associated with a diminished libido, relating to the mental and emotional well-being of an individual.

The mental well-being of concern herein is reflected in the degree of mental activity, mental awareness, drive and energy of the individual. The emotional well-being of concern herein is exhibited in the creativity, enthusiasm and social awareness of the individual. Individuals whose psychic attitudes are diminished are apt to feel "down" or depressed and morose. Individuals having enhanced psychic attitudes are more alert and perceptive; they are better able to perform routine repetitive mental tasks.

Libido is generally recognized to be the result of a complex interaction of factors in which genetic, anatomic, neurologic, psychologic and biochemical factors all play prominent roles. The exact mechanism by which the compounds of the present invention achieve this effect is not understood except to the extent that it is attributable to a biochemical mechanism. Secretions of the endocrine glands are known to affect the psyche. Thus, there is a degree of positive correlation between testosterone blood level changes and dominant or aggressive behavior. Testosterone infusion is also known to improve mental performance in repetitive mental tasks. It has recently been suggested that a dysgenesis of androgen steroids may have a bearing in schizophrenia, cf., Alias, A.G., Lancet, 1248–9, No. 2 (1972).

The fact that libido in both men and women bears a relationship to the endocrine system, and more particularly, to the steroidal hormones associated therewith, has also been previously reported, and is clinically recognized. Physicians are often confronted with patients having a variety of symptoms including those of a diminished libido and related psychasthenia, which may be either organic or psychosomatic in origin. Heretofore, therapy employing the administration or testosterone and its esters, or the orally active 17-methyltestosterone has frequently been employed. Adjunctive androgen therapy is also recommended for the restoration of libido in women with certain gynecologic disturbances and in women who have had oophorectomy and bilateral adrenalectomy. Similarly, androgen therapy has been used to restore libido in impotent men whose impotence has been associated with an endocrine malfunction or insufficiency, as for example, in Addison's disease, castration, diabetes mellitus, eunuchoidism, feminizing interstitial-cell tumors, infantilism and obesity.

Although in some patients such treatment has been effective, it has generally proven to be disappointing due to the physiological side effects of the androgen which soon become apparent. In the female, therapeutic doses of testosterone can produce a virilizing effect including hirsuitism, hoarseness or deepening of the voice and an increase in uterine weight. In the male such symptoms as an increased growth of body hair, an increase in weight of the ventral prostate, enlarged seminal vesicles, increased seminal fluid and sterility have been observed. In striking contrast to the androgens previously utilized for this purpose, the libido of mammals and the psychic attitudes associated therewith in primates are enhanced without any overt, concomitant, androgenic, somatic sideeffects upon the sex accessory structures by the administration of the androst-4-ene-9-ones described in formula (I) above. The castrated rhesus monkey is a useful primate model in which to demonstrate and observe enhanced libidinous behavior. However, the size and temperament of these animals, plus the expense of maintaining large monkey colonies, makes them unsuitable for ordinary routine screening of large numbers of compounds. Whereas the castrated rat is a useful model for the observation of libidinous behavior, the castrated-adrenalectomized rat provides an even higher degree of correlation with primates such as the castrated monkey. The castrated or the castrated-adrenalectomized rat is a more practicable and manageable animal model that can be accommodated in the large numbers required for the successful testing of compounds, and are the standard experimental animals employed for the evaluation of chemical compounds by those skilled in the art.

When administered to castrated or castrated-adrenalectomized rats the 19-hydroxy-androst-4-enes described herein result in both an increase in the number and frequency of mounts, intromissions and ejaculations as compared with castrated control animals. Additionally, there is observed a decrease in the refractory period following emission. This refractory or post-ejaculatory period for the rat refers to the time period following emission and prior to remounting. During this period the male rat is sexually inert and will even resist any sexual advances made by the female. Many observers feel the refractory period provides a more realistic evaluation of libido enhancement. On necropsy of the animals treated, examinations of the secondary sex organs, i.e., the ventral prostate and seminal vesicles, fail to show any overt, peripheral, somatic effects normally associated with androgen administration, and more particularly associated with the administration of testosterone.

The compounds of the present invention can be administered in various unit dosage forms including tablets or lozenges for purposes of absorption through the buccal mucosa. The active ingredient may be enclosed in hard or soft gelatin capsules, or it may be compressed directly into tablets, or they may be incorporated with other pharmaceutical excipients and inert diluents and used in the form of troches, elixirs, suspensions, syrups, wafers, chewing gum and the like. Such compositions and preparations can contain anywhere from 0.1 milligram to about 3 grams of active compound per dosage unit form. Preferably an amount of active ingredient ranging from 0.1 milligram to 500 milligrams is employed per dosage unit. The tablets, troches, pills and capsules may also contain the following pharmaceutical excipients: a binder such as gum tragacanth, acacia, corn starch or gelatin; a diluent such as dicalcium phosphate; a disintegrating agent such as corn starch, potato starch, alginic acid; a lubricant such as magnesium stearate; a sweetening agent such as sucrose, lactose or saccharin, and flavoring agents such as peppermint, oil of wintergreen or cherry flavoring. Various other materials may also be present as coatings or to otherwise modify the physical form of the dosage unit, as for example, shellac-coated tablets or capsules and sugar-coated tablets. Syrups or elixirs may contain the active ingredients, sucrose as a sweetening agent, methyl and propyl parabens as preservatives, and a suitable dye or flavoring agent.

Parenteral fluid dosage forms of injectable forms including those which can be administered by a jet gun are prepared by utilizing the active ingredient in a sterile liquid vehicle such as water or saline solution. Compositions having the desired clarity, stability and adaptability for parenteral use are obtained by dissolving from about 0.1 milligram to about 3 grams of the active ingredient in a vehicle consisting of a mixture of nonvolatile, liquid polyethylene glycols which are soluble in water and organic liquids and which have molecular weights ranging from about 200 to about 1,500. Such solutions may advantageously contain suspending agents, such as sodium carboxymethylcellulose, methylcellulose, polyvinyl pyrrolidone or polyvinyl alcohol. In the case of injectable forms, they may also contain preservatives in the nature of bactericidal and fungicidal agents, as for example, parabens, benzyl alcohol, phenol or thimerosal. If desired, isotonic agents are included such as various sugars or sodium chloride. Adjuvants include local anesthetics and stabilizing or buffering agents may also be usefully employed.

The active ingredient can also be compressed into pellets or small cylinders and implanted subcutaneously or intramuscularly as depot injections or implants. Implants may employ inert materials such as biodegradable polymers or synthetic silicones, as for example, Silastic, silicone rubber manufactured by the Dow-Corning Corporation. Implantation results in a slow but, nevertheless, predictable rate of absorption from the site of implantation.

The following preparations and examples are illustrative of the preparation of the novel compounds and compositions of the present invention, but are not to be construed as necessarily limiting the scope thereof.

EXAMPLE 1

19-(Trimethylsiloxy)-4-androstene-3,17-dione

A mixture of 9.0 gm (0.03 mole) of 19-hydroxy-4-androstene-3,17-dione, 4.3 gm (0.04 mole) of trimethylchlorosilane and 3.2 gm (0.04 mole) of pyridine is refluxed in 100 ml of benzene for a period of 18 hours. The resulting suspension is filtered, the volatiles removed in vacuo and concentrated to a yellow oil. The oil is placed upon a silica gel chromatographic column packed in chloroform and eluted with chloroform. The chloroform eluate is evaporated to dryness in vacuo and the residue is recrystallized twice from hexane to yield the desired 19-(trimethylsiloxy)-4-androstene-3,17-dione having a m.p. of 87°-9° C., uv max (MeOH) 242 nm (ε14,700).

Following essentially the same procedure but substituting triethylchlorosilane and tripropylchlorosilane for the trimethylchlorosilane above results in the formation of 19-(triethylsiloxy)-4-androstene-3,17-dione and 19-(tripropylsiloxy)-4-androstene-3,17-dione, respectively.

Substituting 19-hydroxy-1β-methyl-4-androstene-3,17-dione and 19-hydroxy-6α-methyl-4-androstene-3,17-dione for the 19-hydroxy-4-androstene-3,17-dione above results in the formation of 1β-methyl-19-trimethylsiloxy-4-androstene-3,17-dione and 6α-methyl-19-trimethylsiloxy-4-androstene-3,17-dione.

EXAMPLE 2

19-(Triphenylsiloxy)-4-androstene-3,17-dione

A solution of 9.0 gm (0.03 mole) of 19-hydroxy-4-androstene-3,17-dione, 11.8 gm (0.04 mole) of triphenylchlorosilane and 9.6 gm (0.12 mole) of pyridine contained in 100 ml of benzene is refluxed for a period of 18 hours. The resulting suspension is filtered and concentrated in vacuo to a yellow oil. The oil is placed on a silica gel chromatographic column packed in chloroform which is further eluted with chloroform. The chloroform eluant is evaporated to dryness in vacuo and recrystallized from methanol to yield 19-(triphenylsiloxy)-4-androstene-3,17-dione methanolate having a m.p. of 100°-2° C., uv max (MeOH) 223 nm (ε30,430), 242 nm (ε17,300).

Following essentially the same procedure but substituting 19-hydroxy-1β-methyl-4-androstene-3,17-dione and 19-hydroxy-6α-methyl-4-androstene-3,17-dione for the 19-hydroxy-4-androstene-3,17-dione above results in the preparation of 1β-methyl-19-triphenylsiloxy-4-androstene-3,17-dione and 6α-methyl-19-triphenylsiloxy-4-androstene-3,17-dione.

EXAMPLE 3

3β,17β,19-Tri(trimethylsiloxy)androst-4-ene

Androst-4-ene-3β,17β,19-triol is dissolved in dry pyridine and trimethylsilylacetamide added thereto. The reaction is completed at room temperature within a few minutes. The pyridine is removed under reduced pressure and the residue purified from an acetone-hexane solution to yield the desired 3β,17β,19-tri(trimethylsiloxy)androst-4-ene.

Following essentially the same procedure but substituting 1α-methyl-4-androstene-17β,19-diol, 1α-methyl-4-androstene-3β,17β,19-triol and 7α-methyl-4-androstene-3β,17β,19-triol for the androst-4-ene-3β,17β,19-triol above results in the formation of 1α-methyl-17β,19-di(trimethylsiloxy)androst-4-ene, 1α-methyl-3β,17β,19-tri(trimethylsiloxy)androst-4-ene and 7α-methyl-3β,17β,19-tri(trimethylsiloxy)-4-androstene, respectively.

EXAMPLE 4

17β,19-Di-(1'-ethoxy-1'-cyclohexyloxy)-androst-4-en-3-one

A suspension of 17β,19-dihydroxyandrost-4-en-3-one in anhydrous dioxane is treated at room temperature with pyridine p-toluenesulfonate and cyclohexanone ethyl enolether. The steroid dissolves and a new precipitate forms which upon standing overnight is filtered and recrystallized from methanol-methylene chloride to yield the desired 17β,19-di-(1'-ethoxy-1'-cyclohexyloxy) androst-4-en-3-one.

Using essentially the same procedure but substituting 17β,19-dihydroxy-1α,7α-dimethyl-4-androsten-3-one and 17β,19-dihydroxy-7α-methyl-4-androsten-3-one for the 17β,19-dihydroxyandrost-4-en-3-one above results in the preparation of 17β,19-di-(1'-ethoxy-1'-cyclohexyloxy)-1α,7α-dimethyl-4-androsten-3-one and 17β,19-di-(1'-ethoxy-1'-cyclohexyloxy)-7α-methyl-4-androsten-3-one.

EXAMPLE 5

17β,19-Di(1'-cyclohexenyloxy)androst-4-en-3-one

17β,19-Di-(1'-ethoxy-1'-cyclohexyloxy)androst-4-en-3-one is dissolved in dimethylformamide containing a drop of pyridine. The solution is heated at 150° C. for 1 hour allowing the alcohol which forms to distill out. The solvent is removed under vacuum and the residue recrystallized from methanol to yield the desired 17β,19-di(1'-cyclohexenyloxy)androst-4-en-3-one.

In essentially the same manner substituting 17β,19-di(1'-ethoxy-1'-cyclohexyloxy)-1α,7α-dimethyl-4-androsten-3-one and 17β,19-di-(1'-ethoxy-1'-cyclohexyloxy)-7α-methyl-4-androsten-3-one for the 17β,19-di-(1'-ethoxy-1'-cyclohexyloxy)androst-4-en-3-one above results in the formation of 17β,19-di-(1'-cyclohexenyloxy)-1α,7α-dimethyl-4-androsten-3-one and 17β,19-di-(1'-cyclohexenyloxy)-7α-methyl-4-androsten-3-one.

EXAMPLE 6

17β,19-Di-(1'-cyclohexenyloxy)androst-4-en-3β-ol

17β,19-di-(1'-cyclohexenyloxy)androst-4-en-3-one is dissolved in anhydrous ether and added to a suspension of lithium aluminum hydride in anhydrous ether. After stirring for a period of 16 hours, water is cautiously added. The resulting mixture is filtered, dried over magnesium sulfate and concentrated in vacuo. The residue is crystallized from methanol to yield the desired 17β,19-di-(1'-cyclohexenyloxy)androst-4-en-3β-ol.

In the same manner substituting 17β,19-di-(1'-cyclohexenyloxy)-1α,7α-dimethyl-4-androsten-3-one and 17β,19-di-(1'-cyclohexenyloxy)-7α-methyl-4-androsten-3-one for the 17β,19-di-(1'-cyclohexenyloxy)androst-4-en-3-one above, results in the preparation of 17β,19-di-(1'-cyclohexenyl-oxy)-1α,7α-dimethyl-4-androsten-3β-ol and 17β,19-di-(1'-cyclohexenyloxy)-7α-methyl-4-androsten-3β-ol.

EXAMPLE 7

17α-Methyl-17β,19-di-(2'-tetrahydropyranyloxy)androst-4-en-3-one

17β,19-Dihydroxy-17α-methylandrost-4-en-3-one, phosphoryl chloride and 2,3-dihydropyran are permitted to stand for a period of 16 hours at room temperature. The reaction mixture is diluted with ether, washed with an aqueous sodium carbonate solution, followed by a water wash, dried over sodium sulfate, and evaporated to dryness under vacuum. Crystallization of the residue from methanol results in the formation of 17α-methyl-17β,19-di-(2'-tetrahydropyranyloxy)androst-4-en-3-one.

Following essentially the same procedure but substituting 17β,19-dihydroxy-4,6α,17α-trimethyl-4-androsten-3-one, 17β,19-dihydroxy-4,17α-dimethyl-4-androsten-3-one and 17β,19-dihydroxy-6α,17α-dimethyl-4-androsten-3-one for the 17β,19-dihydroxy-17α-methylandrost-4-en-3-one above, results in the formation 4,6α,17α-trimethyl-17β,19-di-(2'-tetrahydropyranyloxy)androst-4-en-3-one, 4,17α-dimethyl-17β,19-di-(2'-tetrahydropyranyloxy)androst-4-en-3-one and 6α,17α-dimethyl-17β,19-di-(2'-tetrahydropyranyloxy)androst-4-en-3-one, respectively.

EXAMPLE 8

17α-Methyl-17β,19-di-(2'-tetrahydropyranyloxy)androst-4-en-3β-ol

An ether solution of 17α-methyl-17β,19-di-(2'-tetrahydropyranyloxy)androst-4-en-3-one is added to a lithium aluminum hydride suspension in ether. After refluxing for 1 hour, the excess hydride is cautiously decomposed with water. The ether solution is separated, dried over sodium sulfate and concentrated under vacuum. The remaining residue is recrystallized from methanol to yield the desired 17α-methyl-17β,19-di-(2'-tetrahydropyranyloxy)androst-4-en-3β-ol.

Following essentially the same procedure but substituting 4,6α,17α-trimethyl-17β,19-di-(2'-tetrahydropyranyloxy)androst-4-en-3-one, 4,17α-dimethyl-17β,19-di-(2'-tetrahydropyranyloxy)androst-4-en-3-one and 6α,17α-dimethyl-17β,19-di-(2'-tetrahydropyranyloxy)androst-4-en-3-one for the 17α-methyl-17β,19-di-(2'-tetrahydropyranyloxy)androst-4-en-3-one above, results in the preparation of 4,6α,17α-trimethyl-17β,19-di-(2'-tetrahydropyranyloxy)androst-4-en-3β-ol, 4,17α-dimethyl-17β,19-di-(2'-tetrahydropyranyloxy)androst-4-en-3β-ol, and 6α,17α-dimethyl-17β,19-di-(2'-tetrahydropyranyloxy)androst-4-en-3β-ol, respectively.

EXAMPLE 9

17α-Propynyl-17β,19-di-(trimethylsiloxy)androst-4-en-3-one

17β,19-Dihydroxy-17α-propynyl-androst-4-en-3-one, trimethylchlorosilane, and pyridine are refluxed in toluene for a period of 18 hours. The resulting suspension is filtered, and the toluene removed under vacuum. The remaining residue is recrystallized from hexane to yield the desired 17α-propynyl-17β,19-di-(trimethylsiloxy)androst-4-en-3-one.

Substituting 17β,19-dihydroxy-6α,17α-dimethyl-4-androsten-3-one for the 17β,19-dihydroxy-17α-propynylandrost-4-en-3-one above, results in the preparation of 6α,17α-dimethyl-17β,19-di-(trimethylsiloxy)androst-4-en-3-one.

EXAMPLE 10

19-Methoxyandrost-4-ene-3,17-dione

19-Hydroxyandrost-4-ene-3,17-dione is dissolved in methylenechloride and trimethyloxonium fluoroborate added. After stirring at room temperature for a period of two hours, water is added to the reaction mixture, the organic layer is separated, dried over magnesium sulfate and the solvent removed under vacuum. The residue is crystallized from an acetone-hexane solution to yield the desired 19-methoxyandrost-4-ene-3,17-dione.

Using essentially the same procedure but substituting 19-hydroxy-1β-methyl-4-androstene-3,17-dione and 19-hydroxy-6α-methyl-4-androstene-3,17-dione for the 19-hydroxyandrost-4-ene-3,17-dione above results in the formation of 19-methoxy-1β-methyl-4-androstene-3,17-dione and 19-methoxy-6α-methyl-4-androstene-3,17-dione.

EXAMPLE 11

19-Methoxyandrost-4-ene-3β,17β-diol

19-Methoxyandrost-4-ene-3,17-dione is dissolved in methanol and the solution cooled to 0° C. Sodium borohydride is added over a period of fifteen minutes and stirring continued for an additional 2 hours. The solution is poured into water containing a few drops of acetic acid. The white precipitate which forms is collected by filtration, dried and crystallized from acetone to yield the desired 19-methoxy-androst-4-ene-3β,17β-diol.

Substituting 19-methoxy-1β-methyl-4-androstene-3,17-dione and 19-methoxy-6α-methyl-4-androstene-3,17-dione results in the preparation of 19-methoxy-1β-methyl-4-androstene-3β,17β-diol and 19-methoxy-6α-methyl-4-androstene-3β,17β-diol.

EXAMPLE 12

19-Methoxyandrost-4-ene-3β,17β-diol diacetate

19-Methoxyandrost-4-ene-3β,17β-diol is dissolved in a mixture of acetic anhydride and pyridine and the solution allowed to stand overnight at room temperature. The solvents are removed under vacuum and the remaining residue crystallized from acetone-hexane to yield 19-methoxyandrost-4-ene-3β,17β-diol diacetate.

Substituting 19-methoxy-1β-methyl-4-androstene-3β,17β-diol and 19-methoxy-6α-methyl-4-androstene-3β,17β-diol in lieu of the 19-methoxyandrost-4-ene-3β,17β-diol above results in the preparation of 19-methoxy-1β-methyl-4-androstene-3β,17β-diol diacetate and 19-methoxy-6α-methyl-4-androstene-3β,17β-diol diacetate.

EXAMPLE 13

3β,17β-Di-(1'-cyclopentenyloxy)-19-methoxyandrost-4-ene

To a solution of 19-methoxyandrost-4-ene-3β,17β-diol in anhydrous benzene containing p-toluenesulfonic acid is added cyclopentanone diethylketal. The mixture is heated for a period of 1 hour permitting distillation of the alcohol which forms. After the addition of pyridine, the benzene is removed under vacuum and the residue which remains is recrystallized from methanol to yield the desired 3β,17β-di-(1'-cyclopentenyloxy)-19-methoxyandrost-4-ene.

Using the same procedure and substituting 19-methoxy-1β-methyl-4-androstene-3β,17β-diol and 19-methoxy-6α-methyl-4-androstene-3β,17β-diol for the 19-methoxyandrost-4-ene-3β,17βdiol above results in the preparation of 3β,17β-di-(1'-cyclopentenyloxy)-19-methoxy-1β-methyl-4-androstene and 3β,17β-di-(1'-cyclopentenyloxy)-19-methoxy-6α-methyl-4-androstene.

EXAMPLE 14

Androst-4-ene-3β,17β,19-triol 17,19-diacetate

To a solution of lithium tri-t-butoxy-aluminum hydride in tetrahydrofuran is added a tetrahydrofuran solution of 17β,19-dihydroxyandrost-4-en-3-one diacetate. The resulting mixture is stirred at 20° C. for a period of 18 hours after which is added an aqueous solution of sodium potassium tartrate. The mixture is filtered and concentrated to a small volume under reduced pressure. The concentrate is taken up in ether and washed well with water. The combined ether extracts are dried over magnesium sulfate, filtered and the ether removed under vacuum to yield a residue which when recrystallized from a mixture of acetone-hexane results in the preparation of the desired androst-4-ene-3β,17β,19-triol 17,19-diacetate.

Substituting 17β,19-hydroxy-1α-methyl-4-androsten-3-one dipropionate for the 17β,19-dihydroxyandrost-4-en-3-one diacetate above, results in the formation of 1α-methyl-4-androstene-3β,17β,19-triol 17,19-dipropionate.

EXAMPLE 15

3β-(2'-Tetrahydropyranyloxy)androst-4-ene17β,19-diol diacetate

A solution of androst-4-ene-3β,17β,19-triol 17,19-diacetate, p-toluenesulfonic acid and 2,3-dhydropyran are stirred for a period of 3 hours at room temperature. The solution is diluted with ether, washed with an aqueous sodium carbonate solution, washed well with water, dried over sodium sulfate and evaporated to dryness under reduced pressure. Crystallization of the residue from a mixture of acetone-hexane results in the preparation of the desired 3β-(2'-tetrahydropyranyloxy)androst-4-ene-17β,19-diol acetate.

Substituting 1α-methyl-4-androstene-3β,17β,19-triol 17,19-dipropionate for the androst-4-ene-3β,17β,19-triol 17,19-diacetate above results in the preparation of 1α-methyl-3β-(2'-tetrahydropyranyloxy)-4-androstene-17β,19-diol dipropionate.

EXAMPLE 16

3β-(2'-Tetrahydropyranyloxy)androst-4-ene-17β,19-diol

A solution of 3β-(2'-tetrahydropyranyloxy)androst-4-ene-17β,19-diol diacetate in methanol, is refluxed for a period of two hours with an aqueous solution of sodium carbonate. The solvent is removed and the residue so obtained is purified by crystallization from methanol to form the desired 3β-tetrahydropyranyloxy-androst-4-ene-17β,19-diol.

Substituting 1α-methyl-3β-(2'-tetrahydropyranyloxy)-4-androstene-17β,19-diol dipropionate in the above procedure for 3β-(2'-tetrahydropyranyloxy)androst-4-ene-17β,19-diol diacetate results in the preparation of 1α-methyl-3β-(2'-tetrahydropyranyloxy)-4-androstene-17β,19-diol.

EXAMPLE 17

Androst-4-ene-3β,17β,19-triol 19-acetate

A tetrahydrofuran solution of 19-hydroxyandrost-4-ene-3,17-dione acetate is added to lithium tri-t-butoxyaluminum hydride in tetrahydrofuran and the resultant solution stirred overnight at room temperature. An aqueous solution of sodium potassium tartrate is added with stirring until a readily filterable precipitate forms. The filtrate is concentrated under reduced pressure and diluted with ether. The resulting solution is washed with water, dried over magnesium sulfate, and the ether removed under vacuum. The residual androst-4-ene-3β,17β,19-triol 19-acetate so obtained is recrystallized from acetone.

Substituting 19-hydroxy-1β-methyl-4-androstene-3,17-dione acetate and 19-hydroxy-6α-methyl-4-androstene-3,17-dione acetate for 19-hydroxyandrost-4-ene-3,17-dione acetate in the above procedure results in the formation of 1β-methyl-4-androstene-3β,17β,19-triol 19-acetate and 6α-methyl-4-androstene-3β,17β,19-triol 19-acetate.

EXAMPLE 18

3β,17β-Di-(triphenylsiloxy)androst-4-en-19-ol acetate.

A solution of androst-4-ene-3β,17β,19-triol 19-acetate, triphenylchlorosilane, pyridine and toluene are refluxed for a period of 24 hours. The resulting solid is filtered and the volatile materials are removed under vacuum. The resultant oil is purified from methanol to yield the desired 3β,17β-di-(triphenylsiloxy)androst-4-en-19-ol acetate.

Substituting 1β-methyl-4-androstene-3β,17β,19-triol 19-acetate and 6α-methyl-4-androstene-3β,17β,19-triol 19-acetate for the androst-4-ene-3β,17β,19-triol 19-acetate above, results in the preparation of 1β-methyl-3β,17β-di-(triphenylsiloxy)-4-androsten-19-ol acetate and 6α-methyl-3β,17β-di-(triphenylsiloxy)-4-androsten-19-ol acetate.

EXAMPLE 19

3β,17β-Di-(triphenylsiloxy)androst-4-en-19-ol

To an ether solution of 3β,17β-di-(triphenylsiloxy)androst-4-en-19-ol acetate is added a suspension of lithium aluminum hydride in ether. After refluxing for a period of one hour, water is cautiously added, the ether solution is separated, dried over sodium sulfate and evaporated under reduced pressure. The residue when purified from an acetone-hexane mixture results in the preparation of the desired 3β,17β-di-(triphenylsiloxy)androst-4-en-19-ol.

Following the same procedure and substituting 1β-methyl-3β,17β-di-(triphenylsiloxy)-4-androsten-19-ol acetate and 6α-methyl-3β,17β-di-(triphenylsiloxy)-4-androsten-19-ol acetate for the 3β,17β-di-(triphenylsiloxy)androst-4-en-19-ol acetate above results in the preparation of 1β-methyl-3β,17β-di-(triphenylsiloxy)-4-androsten-19-ol and 6α-methyl-3β,17β-di-(triphenylsiloxy)-4-androsten-19-ol, respectively.

EXAMPLE 20

17β-Hydroxy-19-(1'-methoxycyclopentyloxy)androst-4-en-3-one acetate

To a suspension of 17β,19-dihydroxyandrost-4-en-3-one 17-acetate in dioxane is added with stirring a mixture of cyclopentanone methylenol ether and pyridine p-toluenesulfonate. The steroid quickly dissolves and a new precipitate forms which, after standing overnight, is collected and recrystallized from a methanol-methylene chloride mixture to yield the desired 17β-hydroxy-19-(1'-methoxycyclopentyloxy)androst-4-en-3-one acetate.

Following essentially the same procedure but substituting 17β,19-dihydroxy-7α-methyl-4-androsten-3-one 17-acetate, 17β,19-dihydroxy-1α,7α-dimethyl-4-androsten-3-one 17-acetate and 17β,19-dihydroxy-1α-methyl-4-androsten-3-one 17-acetate for the 17β,19-dihydroxyandrost-4-en-3-one 17-acetate above results in the formation of 17β-hydroxy-19-(1'-methoxycyclopentyloxy)-7α-methyl-4-androsten-3-one acetate, 17β-hydroxy-19-(1'-methoxycyclopentyloxy)-1α,7α-dimethyl-4-androsten-3-one acetate and 17β-hydroxy-19-(1'-methoxycyclopentyloxy)-1α-methyl-4-androsten-3-one acetate.

EXAMPLE 21

19-(1'-Cyclopentenyloxy)-17β-hydroxyandrost-4-en-3-one acetate

17β-Hydroxy-19-(1'-methoxycyclopentyloxy)androst-4-en-3-one acetate is dissolved in a dimethylformamide solution containing a drop of pyridine. The solution is refluxed permitting the alcohol which forms to distill. After 1 hour, the remaining solvent is removed under reduced pressure and the remaining residue is recrystallized from methanol to yield the desired 19-(1'-cyclopentenyloxy)-17β-hydroxyandrost-4-en-3-one acetate.

Substituting 17β-hydroxy-19-(1'-methoxycyclopentyloxy)-7α-methyl-4-androsten-3-one acetate, 17β-hydroxy-19-(1'-methoxycyclopentyloxy)-1α,7α-dimethyl-4-androsten-3-one acetate and 17β-hydroxy-19-(1'-methoxycyclopentyloxy)-1α-methyl-4-androsten-3-one acetate for the 17β-hydroxy-19-(1'-methoxycyclopentyloxy)androst-4-en-3-one acetate above results in the formation of 19-(1'-cyclopentenyloxy)-17β-hydroxy-7α-methyl-4-androsten-3-one acetate, 19-(1'-cyclopentenyloxy)-17β-hydroxy-1α,7α-dimethyl-4-androstene-3-one acetate and 19-(1'-cyclopentenyloxy)-17β-hydroxy-1α-methyl-4-androsten-3-one acetate, respectively.

EXAMPLE 22

19-(1'-Cyclopentenyloxy)-androst-4-en-3β,17β-diol 19-(1'-Cyclopentenyloxy)-17β-hydroxyandrost-4-en-3-one acetate is dissolved in anhydrous ether and added to a suspension of lithium aluminum hydride in anhydrous ether. After refluxing for a period of 1 hour, water is cautiously added and the mixture filtered. The organic layer is separated and dried over sodium sulfate. The dried solution is filtered, concentrated in vacuo and the residue recrystallized from methanol to yield the desired 19-(1'-cyclopentenyloxy)androst-4-ene-3β,17β-diol.

Substituting 19-(1'-cyclopentenyloxy)-17β-hydroxy-7α-methyl-4-androsten-3-one acetate, 19-(1'-cyclopentenyloxy)-17β-hydroxy-1α,7α-dimethyl-4-androsten-3-one acetate and 19-(1'-cyclopentenyloxy)-17β-hydroxy-1α-methyl-4-androsten-3-one acetate for the 19-(1'-cyclopentenyloxy)-17β-hydroxyandrost-4-en-3-one acetate above results in the formation of 19-(1'-cyclopentenyloxy)-7α-methyl-4-androsten-3β,17β-diol, 19-(1'-cyclopentenyloxy)-1α,7α-dimethyl-4-androsten-3β,17β-diol and 19-(1'-cyclopentenyloxy)-1α-methyl-4-androsten-3β,17β-diol.

EXAMPLE 23

17β,19-Dihydroxyandrost-4-en-3-one 19-acetate

A tetrahydrofuran solution of 19-hydroxyandrost-4-ene-3,17-dione acetate is added to a mixture of lithium tri-t-butoxyaluminum hydride contained in tetrahydrofuran. After stirring at room temperature overnight, an aqueous solution of potassium sodium tartrate is added with stirring to form a readily filterable white solid. The reaction mixture is filtered and the filtrate dried over magnesium sulfate. The dried solution is filtered and the volatile materials removed in vacuo. The remaining residue is dissolved in chloroform and stirred overnight with activated magnesium dioxide. The mixture is filtered and the filtrate concentrated under reduced pressure. The residue so obtained is crystallized from an acetonehexane mixture to yield the desired 17β,19-dihydroxyandrost-4-en-3-one 19-acetate.

Substituting 19-hydroxy-1β-methyl-androst-4-ene-3,17-dione acetate and 19-hydroxy-6α-methyl-androst-4-ene-3,17-dione acetate for the 19-hydroxyandrost-4-ene-3,17-dione acetate above results in the formation of 17β,19-dihydroxy-1β-methylandrost-4-ene-3-one 19-acetate and 17β,19-dihydroxy-6α-methylandrost-4-en-3-one 19-acetate.

EXAMPLE 24

19-Hydroxy-17β-(1'-methoxycyclohexyloxy)-androst-4-en-3-one acetate

To a suspension of 17β,19-dihydroxyandrost-4-en-3-one 19-acetate in anhydrous dioxane is added cyclohexanone methyl enolether and pyridine p-toluenesulfonate. After standing overnight, the precipitate which forms is collected and crystallized from methanol to give the desired 19-hydroxy-17β-(1'-methoxycyclohexyloxy)androst-4-en-3-one acetate.

Substituting 17β,19-dihydroxy-1β-methylandrost-4-en-3-one 19-acetate and 17β,19-dihydroxy-6α-methylandrost-4-en-3-one 19-acetate for the 17β,19-dihydroxyandrost-4-en-3-one 19-acetate above results in the formation of 19-hydroxy-17β-(1'-methoxycyclohexyloxy)-1β-methylandrost-4-en-3-one acetate and 19-hydroxy-17β-(1'-methoxycyclohexyloxy)-6α-methylandrost-4-en-3-one acetate.

EXAMPLE 25

19-Hydroxy-17β-(1'-methoxycyclohexyloxy)-androst-4-en-3-one

A solution of 19-hydroxy-17β-(1'-methoxycyclohexyloxy)androst-4-en-3-one acetate in aqueous methanol containing sodium carbonate is refluxed for a period of 2 hours. The solution is poured into water, extracted with methylene chloride, the organic layers separated, combined and dried over magnesium sulfate. The filtrate is evaporated in vacuo and the residue recrystallized from methanol resulting in the formation of the desired 19-hydroxy-17β-(1'-methoxycyclohexyloxy)androst-4-en-3-one.

Following essentially the same procedure and substituting 19-hydroxy-17β-(1'-methoxycyclohexyloxy)-β-methylandrost-4-en-3-one acetate and 19-hydroxy-17β-(1'-methoxycyclohexyloxy)-6α-methylandrost-4-en-3-one acetate for the 19-hydroxy-17β-(1'-methoxycyclohexyloxy)androst-4-en-3-one acetate above, results in the preparation of 19-hydroxy-17β-(1'-methoxycyclohexyloxy)-1β-methylandrost-4-en-3-one and 19-hydroxy-17β-(1'-methoxycyclohexyloxy)-6α-methylandrost-4-en-3-one, respectively.

EXAMPLE 26

19-t-Butyldimethylsiloxy-4-androstene-3,17-dione

19-Hydroxy-4-androstene-3,17-dione, t-butyldimethylsilylchloride and pyridine are mixed in dry dimethylformamide and heated on a steam bath overnight. The reaction mixture is poured onto water and stirred well for 15 minutes. The resulting solid is filtered and dissolved in methylenechloride, dried over magnesium sulfate and the solvent removed. The residue is crystallized from an acetone-hexane solution to yield 19-t-butyldimethylsiloxy-4-androstene-3,17-dione.

Following essentially the same procedure and substituting 19-hydroxy-6α-methyl-4-androstene-3,17-dione for the 19-hydroxy-4-androstene-3,17-dione above results in the preparation of 19-t-butyldimethylsiloxy-6α-methyl-4-androstene-3,17-dione.

EXAMPLE 27

19-(4'-Tetrahydropyranyloxy)androst-4-ene-3,17-dione

19-Hydroxy-4-androstene-3,17-dione is dissolved in dimethylformamide and heated to 50° C. 4-Bromotetrahydropyran is added to this solution followed by the addition of sodium hydride. Heating and stirring is continued for a period of 4 hours, the reaction mixture cooled and poured onto ice water. The resulting oil which forms is extracted with ether and the combined ether extracts are washed with water, dried over magnesium sulfate and concentrated to leave a cream-colored solid. Crystallization of this residue from hexane gives pure 19-(4'-tetrahydropyranyloxy)androst-4-ene-3,17-dione.

Following essentially the same procedure but substituting 19-hydroxy-1β-methylandrost-4-ene-3,17-dione and 19-hydroxy-6α-methyl-4-androstene-3,17-dione for the 19-hydroxy-4-androstene-3,17-dione above, accordingly results in the preparation of 1β-methyl-19-(4'-tetrahydropyranyloxy)androst-4-ene-3,17-dione and 6α-methyl-19-(4'-tetrahydropyranyloxy)androst-4-ene-3,17-dione.

EXAMPLE 28

4-Methyl-17β,19-di-(4'-tetrahydropyranyloxy)-4-androsten-3-one

17β,19-Dihydroxy-4-methyl-4-androsten-3-one and 4-bromotetrahydropyran are heated to 50° in dimethylformamide. Sodium hydride is added slowly and stirring at 50° C. is continued for a period of 18 hours. The reaction mixture is poured onto ice water and the water extracted with ether. The combined ether extracts are washed with water, dried over magnesium sulfate and concentrated to dryness. The residue remaining is crystallized from hexane to yield 4-methyl-17β,19-di-(4'-tetrahydropyranyloxy)-4-androsten-3-one.

Following the same procedure and substituting 17β,19-dihydroxy-4-androsten-3-one, 17β,19-dihydroxy-1α-methyl-4-androsten-3-one and 17β,19-dihydroxy-7α-methyl-4-androsten-3-one for the 17β,19-dihydroxy-4-methyl-4-androsten-3-one above, results in the formation of 17β,19-di-(4'-tetrahydropyranyloxy)-4-androsten-3-one, 1α-methyl-17β,19-di-(4'-tetrahydropyranyloxy)-4-androsten-3-one and 7α-methyl-17β,19-di-(4'-tetrahydropyranyloxy)-4-androsten-3-one, respectively.

EXAMPLE 29

1α-Methyl-4-androstene-17β,19-diol

17β,19-Dihydroxy-1α-methyl-4-androsten-3-one in acetic acid is treated with ethanedithiol and p-toluenesulfonic acid. After 4 hours at room temperature, the solution is poured onto water and the mixture extracted with methylenechloride. The methylenechloride extracts are washed well with water, sodium hydroxide solution, water, dried over sodium sulfate and evaporated under reduced pressure to leave 17β,19-dihydroxy-1α-methyl-4-androsten-3-one 3-ethylenethioketal which is recrystallized once from a solution of acetone-hexane.

Raney nickel is added to a solution of 17β,19-dihydroxy-1α-methyl-4-androsten-3-one 3-ethylenethioketal in methanol and the resulting suspension is refluxed for 4 hours with rapid stirring. The suspension is cooled, filtered and the solvent evaporated. The remaining residue is chromatographed on silica gel an eluted with methylenechloride. Recrystallization from acetone-hexane yields the compound 1α-methyl-4-androstene-17β,19-diol.

Substituting 17β,19-dihydroxy-1α,17α-dimethyl-4-androsten-3-one and 17β,19-dihydroxy-4-methyl-4-androsten-3-one in lieu of the 17β,19-dihydroxy-1α-methyl-4-androsten-3-one above, results in the preparation of 1α,17α-dimethyl-4-androstene-17β,19-diol and 4-methyl-4-androsten-17β,19-diol, respectively.

EXAMPLE 30

1α-Methyl-4-androstene-17β,19-diol dipropionate

1α-Methyl-4-androstene-17β,19-diol is dissolved in pyridine and propionic anhydride and stirred under nitrogen at room temperature overnight. Ethanol is added and stirring continued for an additional 2 hours. The solvents are removed under vacuum and the residue is crystallized from hexane to yield 1α-methyl-4-androstene-17β,19-diol dipropionate.

Substituting 1α,17α-dimethyl-4-androstene-17β,19-diol and 4-methyl-4-androstene-17β,19-diol for the 1α-methyl-4-androstene-17β,19-diol above results in the preparation of 1α,17α-dimethyl-4-androsten-17β,19-diol dipropionate and 4-methyl-4-androstene-17β,19-diol dipropionate

EXAMPLE 31

1α-Methyl-4-androstene-17β,19-diol 17-propionate

To a solution of 1α-methyl-4-androstene-17β,19-diol dipropionate in 10% aqueous methanol is added 1 equivalent sodium bicarbonate and the solution is heated under reflux for one hour. Methanol is removed under vacuum to half volume and the concentrate is poured onto water. The solid is filtered, air dried and crystallized from hexane to give 1α-methyl-4-androstene-17β,19-diol 17-propionate.

Substituting 1α,17α-dimethyl-4-androstene-17β,19-diol dipropionate and 4-methyl-4-androstene-17β,19-diol dipropionate in the above procedure for the 1α-methyl-4-androstene-17β,19-diol dipropionate results in the formation of 1α,17α-dimethyl-4-androsten-17β,19-diol 17-propionate and 4-methyl-4-androstene-17β,19-diol 17-propionate, respectively.

EXAMPLE 32

4-Androstene-3α,17β,19-triol

A 1 M solution of lithium tri-sec-butylborohydride in tetrahydrofuran under nitrogen is cooled in a dry ice-acetone bath to about −78° C. and 17β,19-dihydroxy-4-androsten-3-one in tetrahydrofuran is slowly added. The reaction mixture is stirred for a period of two hours at this temperature, warmed to 0° C. and stirring continued for an additional two hours. The reaction mixture is decomposed by the addition of 3 N sodium hydroxide followed by the addition of a 30% hydrogen peroxide solution. Solid potassium carbonate is added and the tetrahydrofuran solution decanted. The solid residue is washed with fresh tetrahydrofuran and the combined tetrahydrofuran solutions are dried over anhydrous sodium sulfate, filtered, and evaporated. The residue is crystallized from acetone to yield 4-androstene-3α,17β-19-triol.

Following essentially the same procedure and substituting 17β,19-dihydroxy-7α-methyl-4-androsten-3-one diacetate, 7α-methyl-17β,19-di-(2'-tetrahydropyranyloxy)-4-androsten-3-one and 19-hydroxy-1β-methyl-4-androsten-3,17-dione for the 17β,19-dihydroxy-4-androsten-3-one above results in the preparation of 7α-methyl-4-androstene-3α,17β,19-triol 17β,19-diacetate, 7α-methyl-17β,19-di-(2'-tetrahydropyranyloxy)-4-androsten-3α-ol and 1β-methyl-4-androstene-3α,17β,19-triol, respectively.

EXAMPLE 33

7α-Methyl-4-androstene-3α,17β,19-triol

A 0.5 M solution of potassium tri-sec-butylborohydride in tetrahydrofuran under nitrogen is cooled to −78° C. in a dry ice-acetone bath. 17β,19-Dihydroxy-7α-methyl-4-androsten-3-one in tetrahydrofuran is added slowly and the reaction mixture is stirred for a period of 2 hours at this temperature, warmed to 0° C., and stirred for an additional two hours. The reaction mixture is decomposed by the addition of 3 N sodium hydroxide followed by a 30% hydrogen peroxide solution. Solid potassium carbonate is added and the tetrahydrofuran solution decanted. The solid residue is washed with fresh tetrahydrofuran and the combined tetrahydrofuran solutions are dried over anhydrous sodium sulfate, filtered and the filtrate removed by evaporation. The residue is crystallized from acetone to yield 7α-methyl-4-androstene-3α,17β,19-triol.

Substituting 17β,19-dihydroxy-4,17α-dimethyl-4-androsten-3-one and 19-hydroxy-6α-methyl-4-androstene-3,17-dione for 17β,19-dihydroxy-7α-methyl-4-androsten-3-one above results in the preparation of 4,17α-dimethyl-4-androstene-3α,17β,19-triol and 6α-methyl-4-androstene-3α,17β,19-triol, respectively.

EXAMPLE 34

17β,19-Dihydroxy-1,4-androstadien-3-one dipropionate

17β,19-Dihydroxy-4-androsten-3-one dipropionate and dichlorodicyanobenzoquinone are refluxed in anhydrous dioxane for a period of 48 hours. The mixture is cooled and filtered and the filtrate concentrated under vacuum. Methylenechloride is added and the resulting mixture filtered. The filtrate is washed well with water, dried over sodium sulfate and the solvent removed. Chromatography of the residue on silica gel and elution with methylenechloride provides a solid which is crystallized from acetone-hexane to yield the desired 17β,19-dihydroxy-1,4-androstadien-3-one dipropionate.

Substituting 17β,19-dihydroxy-17α-methyl-4-androsten-3-one dipropionate and 17β,19-dihydroxy-6α-methyl-4-androsten-3-one dipropionate for 17β,19-dihydroxy-4-androsten-3-one dipropionate above results in the formation of 17β,19-dihydroxy-17α-methyl-1,4-androstadien-3-one dipropionate and 17β,19-dihydroxy-6α-methyl-1,4-androstadien-3-one dipropionate, respectively.

EXAMPLE 35

17β,19-Dihydroxy-1α-methyl-4-androst-en-3-one dipropionate

A solution of lithium dimethylcopper is prepared under nitrogen by the addition of 1.6 M ethereal methyllithium to an ether slurry of cuprous iodide at 0° C. The solution is stirred at 0° C. for 20 minutes and then a solution of 17β,19-dihydroxy-1,4-androstadien-3-one dipropionate in anhydrous tetrahydrofuran is added slowly and stirred for one-half hour. The mixture is poured onto a saturated aqueous ammonium chloride solution, benzene is added and the resulting mixture filtered through diatomaceous earth. The organic layer is washed with aqueous ammonium chloride, water, dried over magnesium sulfate and evaporated to dryness. The residue is passed through a silica gel column and eluted with benzene. Recrystallization from hexane yields 17β,19-dihydroxy-1α-methyl-4-androsten-3-one dipropionate.

Substituting 17β,19-dihydroxy-17α-methyl-1,4-androstadien-3-one dipropionate and 17β,19-dihydroxy-6α-methyl-1,4-androstadien-3-one dipropionate for 17β,19-dihydroxy-1,4-androstadien-3-one in the above procedure results in the formation of 17β,19-dihydroxy-1α,17α-dimethyl-4-androsten-3-one dipropionate and 17β,19-dihydroxy-1α,6α-dimethyl-4-androsten-3-one dipropionate.

EXAMPLE 36

17β,19-Dihydroxy-1α-methyl-4-androsten-3-one

A solution of 17β,19-dihydroxy-1α-methyl-4-androsten-3-one dipropionate in methanol is refluxed for two hours with aqueous sodium carbonate. The solvent is removed and the residue dissolved in chloroform. The chloroform solution is washed well with water, dried over magnesium sulfate and evaporated under vacuum. The residue which remains in crystallized from acetonitrile to yield 17β,19-dihydroxy-1α-methyl-4-androsten-3-one.

Substituting 17β,19-dihydroxy-1α,7α-dimethyl-4-androsten-3-one dipropionate and 17β,19-dihydroxy-1α,6α-dimethyl-4-androsten-3-one dipropionate in the above procedure results in the preparation of 17β,19-dihydroxy-1α,17α-dimethyl-4-androsten-3-one and 17β,19-dihydroxy-1α,6α-dimethyl-4-androsten-3-one, respectively.

EXAMPLE 37

1α-Methyl-4-androstene-3β,17β,19-triol

17β,19-Dihydroxy-1α-methyl-4-androsten-3-one is dissolved in ethanol and sodium borohydride is added slowly under nitrogen. After stirring at room temperature for 4 hours, the solution is poured onto ice water containing a few drops of acetic acid. The solid which forms is filtered and recrystallized from ethanol to yield 1α-methyl-4-androstene-3β,17β,19-triol.

Substituting 17β,19-dihydroxy-1α,17α-dimethyl-4-androsten-3-one and 17β,19-dihydroxy-1α,6α-dimethyl-4-androsten-3-one for 17β,19-dihydroxy-1α-methyl-4-androsten-3-one above results in the formation of 1α,17α-dimethyl-4-androstene-3β,17β,19-triol and 1α,6α-dimethyl-4-androstene-3β,17β,19-triol, respectively.

EXAMPLE 38

1β,2β-Methylene-4-androstene-3,17-dione

To a solution of potassium t-butoxide in dimethyl-sulfoxide at 25° C. under nitrogen is added 1,4-androstadiene-3,17-dione in dimethylsulfoxide with stirring. After fifteen minutes the mixture is poured onto cold aqueous ammonium chloride. The solid is rapidly filtered, washed well with water and dissolved in ether. The ether solution is washed again with water, dried over sodium sulfate and evaporated at room temperature to yield 1,5-androstadiene-3,17-dione.

A tetrahydrofuran solution of 1,5-androstadiene-3,17-dione is added under nitrogen to a solution of lithium tri-t-butoxyaluminium hydride in tetrahydrofuran. After stirring at room temperature overnight, an aqueous solution of potassium sodium tartrate is added with stirring to form a readily filterable while solid. The reaction mixture is filtered and the filtrate dried over magnesium sulfate and the solvent removed. The residue which remains is recrystallized from acetone to yield 1,5-androstadiene-3β,17β-diol.

To a stirred solution of 1,5-androstadiene-3β,17β-diol in a mixture of dry ether and glyme is added zinc-copper couple and methylene iodide. This reaction mixture is refluxed for 4 hours, cooled to room temperature, diluted with ether and filtered. The filtrate is washed with aqueous sodium chloride, water and dried over anhydrous magnesium sulfate. The ether is removed under reduced pressure and the residue crystallized from acetone-hexane to yield 1β,2β-methylene-5-androstene-3β,17β-diol.

The 1β,2β-methylene-5-androstene-3β,17β-diol is dissolved in acetone and Jones reagent added until a persistent yellow-orange color appears. After stirring at room temperature for ten minutes the mixture is poured onto ice-water and the precipitate is collected by filtration. The precipitate is dissolved in a solution of sodium methoxide in methanol and stirred for a period of 30 minutes at room temperature. The methanol is removed and the residue triturated with water. The solid which results is filtered and crystallized from acetone to yield 1β,2β-methylene-4-androstene-3,17-dione.

EXAMPLE 39

1β-Methyl-4-androstene-3,17-dione

1β,2β-Methylene-4-androstene-3,17-dione, zinc powder, and acetic acid are refluxed together for a period of 1 hour. On cooling benzene is added, the suspension filtered and the filtrate taken to dryness under vacuum. The residue is chromatographed on silica gel and eluted with methylenechloride. Recrystallization from acetone-hexane yields 1β-methyl-4-androstene-3,17-dione.

EXAMPLE 40

1β-Methyl-5-androstene-3β,17β-diol, diacetate

To a solution of potassium t-butoxide in dimethylsulfoxide at 25° C. under nitrogen is added 1β-methyl-4-androstene-3,17-dione in dimethylsulfoxide with stirring. After 15 minutes the mixture is poured onto cold aqueous ammonium chloride. The solid is rapidly filtered, washed well with water and dissolved in ether. The ether is washed with water, dried over sodium sulfate and removed at room temperature to yield 1β-methyl-5-androstene-3,17-dione.

A tetrahydrofuran solution of 1β-methyl-5-androstene-3,17-dione is added under nitrogen to a solution of lithium tri-t-butoxyaluminum hydride in tetrahydrofuran. After stirring at room temperature for a period of 18 hours, an aqueous solution of potassium sodium tartrate is added with stirring to form a readily filterable white solid. The reaction mixture is filtered, the filtrate dried over magnesium sulfate, and the solvent removed. The residue is crystallized from an acetone-hexane solution to yield 1β-methyl-5-androstene-3β,17β-diol.

The 1β-methyl-5-androstene-3β,17β-diol is dissolved in acetic anhydride and pyridine and kept at room temperature for a period of 20 hours. The solvent is removed under vacuum and the residue recrystallized from hexane to yield 1β-methyl-5-androstene-3β,17β-diol diacetate.

EXAMPLE 41

5α-Bromo-1β-methylandrostane-3β,6β,17β-triol 3,17-diacetate

A solution of 1β-methyl-5-androstene-3β,17β-diol, diacetate in ether is cooled to −5° C. in an ice-methanol bath and a solution of aqueous perchloric acid added followed by the addition of N-bromoacetamide. Stirring at −5° C. is continued for a period of two hours followed by the addition of water. The ether layer is washed with water until neutral and concentrated to a small volume at room temperature. The product is filtered and crystallized from a solution of acetone-hexane to yield 5α-bromo-1β-methylandrostane-3β,6β,17β-triol 3,17-diacetate.

Following essentially the same procedure and substituting 4α-methyl-5-androstene-3β,17β-diol, diacetate, 6-methyl-5-androstene-3β,17β-diol, diacetate, 7α-methyl-5-androstene-3β,17β-diol, diacetate and 1β,17α-dimethyl-5-androstene-3β,17β-diol diacetate for the 1β-methyl-5-androstene-3β,17β-diol, diacetate above, results in the formation of 5α-bromo-4α-methylandrostane-3β,6β,17β-triol 3,17-diacetate, 5α-bromo-6-methylandrostane-3β,6β,17β-triol 3,17-diacetate, 5α-bromo-7α-methylandrostane-3β,6β,17β-triol 3,17-diacetate and 5α-bromo-1β,17α-dimethylandrostane-3β,6β,17β-triol 3,17-diacetate, respectively.

EXAMPLE 42

5α-Bromo-1β-methyl-6β,19-oxidoandrostane-3β,17β-diol diacetate

A stirred suspension of lead tetraacetate and calcium carbonate in cyclohexane is refluxed for 30 minutes to which is added iodine and 5α-bromo-1β-methyl-androstane-3β,6β,17β-triol 3,17-diacetate. The stirred mixture is irradiated with a 600 Watt lamp which maintains the mixture at reflux. After the iodine color has disappeared the mixture is cooled, filtered and the residue washed with ether. The filtrates are combined, concentrated to one-fifth volume, washed with a 10% sodium thiosulfate solution, followed by a water wash, dried over magnesium sulfate and evaporated under reduced pressure to a semi-solid residue which is crystallized from acetone-hexane to yield 5α-bromo-1β-methyl-6β,19-oxidoandrostane-3β,17β-diol diacetate.

Following essentially the same procedure and substituting 5α-bromo-4α-methylandrostane-3β,6β,17β-triol 3,17-diacetate, 5α-bromo-6-methylandrostane-3β,6β,17β-triol 3,17-diacetate, 5α-bromo-7α-methylandrostane-3β,6β,17β-triol 3,17-diacetate and 5α-bromo-1β,17α-dimethylandrostane-3β,6β,17β-triol 3,17-diacetate for the 5α-bromo-1β-methyl-androstane-3β,6β,17β-triol 3,17-diacetate above results in the preparation of 5α-bromo-4α-methyl-6β,19-oxidoandrostane-3β,17β-diol diacetate, 5α-bromo-6-methyl-6β,19-oxidoandrostane-3β,17β-diol diacetate, 5α-bromo-7α-methyl-6β,19-oxidoandrostane-3β,17β-diol diacetate and 5α-bromo-1β,17α-dimethyl-6β,19-oxidoandrostane-3β,17β-diol diacetate, respectively.

EXAMPLE 43

5α-Bromo-1β-methyl-6β,19-oxidoandrostane-3β,17β-diol

To a solution of 5α-bromo-1β-methyl-6β,19-oxidoandrostane-3β,17β-diol diacetate in methanol is added a 5% aqueous potassium carbonate solution and the mixture refluxed for a period of about three hours. The methanol is removed and water added. The solid which forms is filtered and crystallized from aqueous methanol to yield 5α-bromo-1β-methyl-6β,19-oxidoandrostane-3β,17β-diol.

Substituting 5α-bromo-4α-methyl-6β,19-oxidoandrostane-3β,17β-diol diacetate, 5α-bromo-6-methyl-6β,19-oxidoandrostane-3β,17β-diol diacetate, 5α-bromo-7α-methyl-6β,19-oxidoandrostane-3β,17β-diol diacetate and 5α-bromo-1β,17α-dimethyl-6β,19-oxidoandrostane-3β,17β-diol diacetate for the 5α-bromo-1β-methyl-6β,19-oxidoandrostane-3β,17β-diol diacetate results in the preparation of 5α-bromo-4α-methyl-6β,19-oxidoandrostane-3β,17β-diol, 5α-bromo-6-methyl-6β,19-oxidoandrostane-3β,17β-diol, 5α-bromo-7α-methyl-6β,19-oxidoandrostane-3β,17β-diol and 5α-bromo-1β,17α-dimethyl-6β,19-oxidoandrostane-3β,17β-diol, respectively.

EXAMPLE 44

5α-Bromo-1β-methyl-6β,19-oxidoandrostane-3,17-dione

5α-Bromo-1β-methyl-6β,19-oxidoandrostane-3β,17β-diol is dissolved in acetone and Jones reagent added until a persistent yellow-orange color appears. Stirring is continued for about 30 minutes whereupon the solution is poured onto water. The solid is filtered and recrystallized from acetone-hexane to yield 5α-bromo-1β-methyl-6β,19-oxidoandrostane-3,17-dione.

Substituting 5α-bromo-4α-methyl-6β,19-oxidoandrostane-3β,17β-diol, 5α-bromo-6-methyl-6β,19-oxidoandrostane-3β,17β-diol, 5α-bromo-7α-methyl-6β,19-oxidoandrostane-3β,17β-diol and 5α-bromo-1β,17α-dimethyl-6β,19-oxidoandrostane-3β,17β-diol for the 5α-bromo-1β-methyl-6β,19-oxidoandrostane-3β,17β-diol above results in the preparation of 5α-bromo-4α-methyl-6β,19-oxidoandrostane-3,17-dione, 5α-bromo-6-methyl-6β,19-oxidoandrostane-3,17-dione, 5α-bromo-7α-methyl-6β,19-oxidoandrostane-3,17-dione and 5α-bromo-17β-hydroxy-1β,17α-dimethyl-6β,19-oxidoandrostane-3-one, respectively.

EXAMPLE 45

19-Hydroxy-1β-methyl-4-androstene-3,17-dione

Zinc powder is added to a solution of 5α-bromo-1β-methyl-6β,19-oxidoandrostane-3,17-dione in ethanol and the mixture heated under reflux with stirring for a period of about 3 hours. The suspension is filtered and the zinc cake washed with hot ethanol. Removal of the solvent from the combined filtrates affords a residue which is recrystallized from an acetone-hexane solution to yield 19-hydroxy-1β-methyl-4-androstene-3,17-dione.

Following essentially the same procedure but substituting 5α-bromo-4α-methyl-6β,19-oxidoandrostane-3,17-dione, 5α-bromo-6-methyl-6β,19-oxidoandrostane-3,17-dione, 5α-bromo-7α-methyl-6β,19-oxidoandrostane-3,17-dione and 5α-bromo-17β-hydroxy-1β,17α-dimethyl-6β,19-oxidoandrostan-3-one for the 5α-bromo-1β-methyl-6β,19-oxidoandrostane-3,17-dione above results in the preparation of 19-hydroxy-4-methyl-4-androstene-3,17-dione, 19-hydroxy-6α-methyl-4-androstene-3,17-dione, 19-hydroxy-7α-methyl-4-androstene-3,17-dione and 17β,19-dihydroxy-1β,17α-dimethyl-4-androstene-3-one, respectively.

EXAMPLE 46

17β,19-Dihydroxy-4,6α,17α-trimethyl-4-androsten-3-one

A mixture of 17β,19-dihydroxy-6α,17α-dimethyl-4-androsten-3-one, thiophenol, 40% aqueous formaldehyde, triethylamine and ethanol is heated under reflux for a period of about 48 hours. The cooled solution is poured into aqueous sodium hydroxide and the product isolated by ether extraction. The ether extract is washed with water and dried over magnesium sulfate. The residue left after evaporation of the ether is triturated with hexane to remove condensation products derived from the thiophenol and formaldehyde. The 17β,19-dihydroxy-6α-methyl-4-phenylthiomethyl-4-androsten-3-one so obtained is desulfurized by dissolving in acetone and adding to a suspension of Raney Nickel in refluxing acetone. The resulting mixture is heated under reflux while stirring for about 5 hours. The hot solution is filtered and the nickel washed with boiling ethanol and water. The combined filtrates are concentrated under vacuum whereupon the product separates as a solid. Recrystallization from acetone-hexane yields 17β,19-dihydroxy-4,6α,17α-trimethyl-4-androsten-3-one.

Following essentially the same procedure and substituting 17β, 19-dihydroxy-4-androsten-3-one, 19-hydroxy-1α-methyl-4-androstene-3,17-dione and 17β,19-dihydroxy-7α-methyl-4-androstene-3-one for the 17β,19-dihydroxy-6α,17α-dimethyl-4-androsten-3-one above results in the preparation of 17β,19-dihydroxy-4-methyl-4-androsten-3-one, 19-hydroxy-1α,4-dimethyl-4-androstene-3,17-dione, and 17β,19-dihydroxy-4,7α-methyl-4-androsten-3-one, respectively.

EXAMPLE 47

17β,19-Dihydroxy-4,17α-dimethyl-4-androsten-3-one

A solution of 17β,19-dihydroxy-17α-methyl-4-androsten-3-one in t-butanol is heated to boiling and added to a boiling solution of potassium t-butoxide in t-butanol. Methyl chloride in t-butanol is slowly added. The solution is cooled, acidified with concentrated hydrochloric acid, and diluted with water. The t-butanol is removed under vacuum and the aqueous layer extracted with ethylacetate. The extract is washed with water, dried over magnesium sulfate and evaporated in vacuo. The residue which remains is chromatographed on silica gel and eluted with ethylacetate. The eluant is crystallized from acetonitrile to yield 17β,19-dihydroxy-4,17α-dimethyl-4-androstene-3-one.

EXAMPLE 48

5α,6α-Epoxy-17α-methyl-androstane-3β,17β,19-triol 3,19-diacetate

A solution of 17α-methyl-5-androstene-3β,17β,19-triol 3,19-diacetate in chloroform is chilled to 0° C. and treated with m-chloroperbenzoic acid in chloroform which is precooled to 0° C. The mixture is stirred and allowed to warm to room temperature. After a period of about 48 hours, the solution is washed with a 10% sodium sulfite solution, a solution of sodium thiosulfate, a sodium bicarbonate solution and water. The chloroform extract is dried over magnesium sulfate and evaporated in vacuo. The residue which remains is crystallized from methanol to give 5α,6α-epoxy-17α-methylandrostane-3β,17β,19-triol 3,19-diacetate.

EXAMPLE 49

6β,17α-Dimethyl-androstane-3β,5α,17β,19-tetrol

Ethereal methylmagnesium bromide is added slowly to a stirred solution of 5α,6α-epoxy-17α-methylandrostane-3β,17β,19-triol 3,19-diacetate in tetrahydrofuran. The solution is heated under reflux for about 24 hours, cooled and poured onto a saturated aqueous ammonium chloride solution. The mixture is extracted with ethylacetate, washed with brine, dried over magnesium sulfate and the solvent removed under reduced pressure. The residue which remains is crystallized from ethyl acetate to yield 6β,17α-dimethylandrostane-3β,5α,17β,19-tetrol.

EXAMPLE 50

17β-Hydroxy-6α,17α-dimethyl-4-androstene-3,19-dione

6β,17α-Dimethylandrostane-3β,5α,17β,19-tetrol is dissolved in acetone and Jones reagent added with stirring. After about 15 minutes the reaction mixture is poured onto water. After stirring for about 30 minutes the solid is filtered and dissolved in methanol containing sodium hydroxide. After about 2 hours the methanol is removed at room temperature and the residue triturated with water. Recrystallization of this residue from an acetone-water solution yields 17β-hydroxy-6α,17α-dimethyl-4-androstene-3,19-dione.

EXAMPLE 51

6α,17α-Dimethyl-4-androstene-3β,17β,19-triol

Sodium borohydride is added under nitrogen with stirring to a solution of 17β-hydroxy-6α,17α-dimethyl-4-androstene-3,19-dione in methanol. After about 5 hours at room temperature, the solution is poured onto water containing a few drops of acetic acid. The solid which forms is filtered and crystallized from methanol to yield 6α,17α-dimethyl-4-androstene-3β,17β,19-triol.

EXAMPLE 52

17β,19-Dihydroxy-6α,17α-dimethyl-4-androsten-3-one

6α,17α-Dimethyl-4-androstene-3β,17β,19-triol is dissolved in hot chloroform and cooled to 15° C. Activated manganese dioxide is added at such a rate that the temperature does not rise above 25° C. Stirring is continued at room temperature for about 1 hour. The manganese dioxide is removed by filtration through diatomaceous earth and the chloroform distilled under vacuum. The residue which remains is crystallized from acetonitrile to yield 17β,19-dihydroxy-6α,17α-dimethyl-4-androsten-3-one.

EXAMPLE 53

6α,17α-Dimethyl-4-androstene-17β,19-diol

17β,19-Dihydroxy-6α,17α-dimethyl-4-androstene-3-one is dissolved in ethane dithiol. Boron trifluoride-etherate is added and after about 30 minutes the reaction mixture is diluted with ether, washed with a 1 N sodium hydroxide solution until the odor is removed and the organic layer dried over magnesium sulfate. Evaporation of the ether leaves a solid which is triturated with hexane. Filtration results in collection of the thioketal which is dissolved in methanol. Raney Nickel is added and the resulting suspension is heated under reflux for about 5 hours while being stirred. On cooling the nickel is removed by filtration and the solvent evaporated. Chromatography of the residue on silica gel, elution with benzene-ethylacetate and crystallization from hexane yields the desired 6α,17α-dimethyl-4-androstene-17β,19-diol.

EXAMPLE 54

19-Acetoxy-5α,6α-epoxy-androstane-3,17-dione bis ethyleneketal

To a solution of 19-acetoxy-5-androstene-3,17-dione bis ethyleneketal in methylenechloride which has been precooled to 0° C. is added a methylenechloride solution of m-chloroperbenzoic acid also precooled to 0° C. The mixture is stirred at room temperature for about 24 hours and additional methylenechloride is added. The methylenechloride solution is washed sequentially with solutions of sodium sulfite, sodium thiosulfate, sodium bicarbonate and finally with water. The methylenechloride extract is dried over magnesium sulfate and taken to dryness under reduced pressure. Recrystallization of the residue from methanol yields 19-acetoxy-5α,6α-epoxy-androstane-3,17-dione bis ethyleneketal.

EXAMPLE 55

5α,19-Dihydroxy-6β-methylandrostane-3,17-dione bis ethyleneketal

A solution of 19-acetoxy-5α,6α-epoxyandrostane-3,17-dione bis ethyleneketal in tetrahydrofuran is added to an ethereal solution of methylmagnesium bromide. The resultant mixture is refluxed for approximately 4 hours, cooled and treated with a saturated aqueous ammonium chloride solution. The organic layer obtained is evaporated, extracted with ethylacetate, washed with brine, dried over magnesium sulfate and concentrated. Crystallization of the residue from a solution of acetone-hexane yields 5α,19-dihydroxy-6β-methylandrostane-3,17-dione bis ethyleneketal.

EXAMPLE 56

19-Hydroxy-6α-methyl-4-androstene-3,17-dione

A solution of 5α,19-dihydroxy-6β-methylandrostane-3,17-dione bis ethyleneketal in methanol containing aqueous sulfuric acid is heated to its reflux temperature and the solvent removed. Crystallization of the residue from an acetone-hexane solution yields 19-hydroxy-6α-methyl-4-androstene-3,17-dione.

EXAMPLE 57

4,6-Androstadiene-3,17,19-trione

19-Hydroxy-4-androstene-3,17-dione and chloranil are dissolved in t-butanol and rapidly brought to reflux. The t-butanol is removed by distillation at atmospheric pressure at such a rate so that the total reflux and distillation time equals one hour. The dark pasty residue is triturated with hot chloroform and cooled. The solid which remains is removed by filtration and the filtrate successively extracted with water, a 2% sodium hydroxide solution and again with water. The organic layer is dried over magnesium sulfate and the solvent removed under vacuum to yield 19-hydroxy-4,6-androstadiene-3,17-dione. The diene so prepared is dissolved in acetone and chilled in an ice bath. Jones reagent is added over a period of about 10 minutes and stirring continued for an additional 45 minutes. The mixture is poured onto water. The solid which forms is filtered and recrystallized from benzene to yield 4,6-androstadiene-3,17,19-trione.

Following essentially the same procedure and substituting 19-hydroxy-4-methyl-4-androstene-3,17-dione, 17β,19-dihydroxy-17α-methyl-4-androsten-3-one and 17β,19-dihydroxy-17α-propinyl-4-androsten-3-one for the 19-hydroxy-4-androstene-3,17-dione above results in the preparation of 4-methyl-4,6-androstadiene-3,17,19-trione, 17β-hydroxy-17α-methyl-4,6-androstadiene-3,19-dione and 17β-hydroxy-17α-propinyl-4,6-androstadiene-3,19-dione.

EXAMPLE 58

7α-Methyl-4-androstene-3β,17β,19-triol

A solution of lithium dimethylcopper is prepared under nitrogen by the addition of 1.6 M ethereal methyllithium to a slurry of cuprous iodide in anhydrous ether at 0° C. The solution is stirred at 0° C. for 20 minutes, a solution of 4,6-androstadiene-3,17,19-trione in anhydrous tetrahydrofuran is added over a period of about 20 minutes and stirring continued for an additional 30 minutes. The mixture is poured onto a saturated aqueous ammonium chloride solution, benzene is added and the resulting mixture is rapidly filtered through diatomaceous earth. The organic layer is washed with an aqueous ammonium chloride solution, water, dried over magnesium sulfate and evaporated to dryness. The crude product is dissolved in aqueous methanol containing a drop of hydrochloric acid. The solution is stirred at room temperature for about 1 hour and poured onto ice-water. The resulting oil is extracted into methylenechloride, washed with water, dried over magnesium sulfate and the solvent removed. The residue which remains is crystallized from ether-hexane to yield 7α-methyl-4-androstene-3,17,19-trione. The trione so prepared is dissolved in ethanol and sodium borohydride added under nitrogen. Stirring is continued for about 1 hour, and the solution poured onto ice water containing a few drops of acetic acid. The solid which forms is filtered, dried and recrystallized from ethanol to yield 7α-methyl-4-androstene-3β, 17β,19-triol.

Substituting 4-methyl-4,6-androstadiene-3,17,19-trione, 17β-hydroxy-17α-methyl-4,6-androstadiene-3,19-dione and 17β-hydroxy-17α-propinyl-4,6-androstadiene-3,19-dione for the 4,6-androstadiene-3,17,19-trione above results in the formation of 4,7α-dimethyl-4-androstene-3β,17β,19-triol, 7α,17α-dimethyl-4-androstene-3β,17β,19-triol and 7α-methyl-17α-propinyl-4-androstene-3β,17β,19-triol, respectively.

EXAMPLE 59

17β,19-Dihydroxy-7α-methyl-4-androsten-3-one

7α-Methyl-4-androstene-3β,17β,19-triol is dissolved in hot chloroform and cooled to 15° C. Activated manganese dioxide is added at a rate such that the temperature does not rise above 25° C. Stirring is continued at room temperature for about 1 hour, the manganese dioxide is removed by filtration through a bed of diatomaceous earth and the chloroform distilled under vacuum. The residue which remains is crystallized from acetonitrile to yield 17β,19-dihydroxy-7α-methyl-4-androsten-3-one.

Substituting 4,7α-dimethyl-4-androstene-3β,17β,19-triol, 7α,17α-dimethyl-4-androstene-3β,17β,19-triol and 7α-methyl-17α-propinyl-4-androstene-3β,17β,19-triol for the 7α-methyl-4-androstene-3β,17β,19-triol above results in the formation of 17β,19-dihydroxy-4,7α-dimethyl-4-androsten-3-one, 17β,19-dihydroxy-7α,17α-dimethyl-4-androsten-3-one and 17β,19-dihydroxy-7α-methyl-17α-propinyl-4-androsten-3-one, respectively.

EXAMPLE 60

7α-Methyl-17β,19-di-(2'-tetrahydropyranyloxy)-4-androsten-3-one

To a stirred solution of 17β,19-dihydroxy-7α-methyl-4-androsten-3one and p-toluenesulfonic acid in anhydrous dioxane is added 2,3-dihydropyran slowly. After 5 minutes, methanolic ammonia is added until the solution is slightly basic. The solvent is removed under vacuum and the residual oil is dissolved in methylenechloride. The methylenechloride solution is extracted with aqueous sodium bicarbonate, dried over sodium sulfate, and concentrated under vacuum. The residue which remains is crystallized from pentane to give 7α-methyl-17β,19-di-(2'-tetrahydropyranyloxy)-4-androsten-3-one.

EXAMPLE 61

17β,19-Dihydroxy-1,4,6-androstatrien-3-one diacetate

17β,19-Dihydroxy-4-androsten-3-one diacetate and chloranil are dissolved in t-butanol which is rapidly brought to its reflux temperature. The t-butanol is removed by distillation at atmospheric pressure at such a rate that the total reflux and distillation time equals 1 hour. The dark residue which remains is triturated with hot chloroform and filtered. The filtrate is extracted with water, a 2% sodium hydroxide solution, again with water, dried over magnesium sulfate and the solvent removed to yield 17β,19-dihydroxy-4,6-androstadiene-3-one diacetate.

The diene so prepared is refluxed with dichlorodicyanobenzoquinone in anhydrous dioxane for about 48 hours. The mixture is cooled, filtered and the filtrate poured onto a mixture of methylenechloride and water. The organic layer is separated, washed with water, dried well over magnesium sulfate and the solvent removed. The dark residue which remains is chromatographed on silica gel and eluted with methylenechloride to yield the desired 17β,19-dihydroxy-1,4,6-androstatrien-3-one diacetate.

EXAMPLE 62

17β,19-Dihydroxy-1α-methyl-4,6-androstadien-3-one diacetate

A solution of lithium dimethylcopper is prepared under nitrogen by the addition of 1.6 M ethereal methyllithium to an ether slurry of cuprous iodide at 0° C. The solution is stirred at 0° C. for 20 minutes, a solution of 17β,19-dihydroxy-1,4,6-androstatrien-3-one diacetate in anhydrous tetrahydrofuran is added over a 20-minute period, and the mixture stirred an additional 30 minutes. The reaction mixture is poured onto a saturated aqueous ammonium chloride solution, benzene is added and the resulting mixture filtered through a bed of diatomaceous earth. The organic layer is washed with aqueous ammonium chloride, water, dried over magnesium sulfate and evaporated to dryness. The residue remaining is crystallized from hexane to yield 17β,19-dihydroxy-1α-methyl-4,6-androstadien-3-one diacetate.

EXAMPLE 63

17β,19-Dihydroxy-1α,7α-dimethyl-4-androsten-3-one diacetate

A solution of 17β,19-dihydroxy-1α-methyl-4,6-androstadien-3-one diacetate in anhydrous tetrahydrofuran is added slowly to an ice cold ethereal solution of lithium dimethylcopper prepared as in the preceding Example. Stirring is continued for 30 minutes and the mixture is poured onto a saturated aqueous ammonium chloride solution. Benzene is added and the mixture filtered through a bed of diatomaceous earth. The organic layer is washed with aqueous ammonium chloride, water, dried over magnesium sulfate and evaporated to dryness. The residue is stirred at room temperature with aqueous methanolic hydrochloric acid for 1 hour and then poured onto ice water. The gum is extracted with ether, washed with water, dried over magnesium sulfate and the ether removed. The residue is chromatographed on silica gel and eluted with benzene. The eluant is recrystallized from hexane to give 17β,19-dihydroxy-1α,7α-dimethyl-4-androsten-3-one diacetate.

EXAMPLE 64

17β,19-Dihydroxy-1α,7α-dimethyl-4-androsten-3-one

17β,19-Dihydroxy-1α,7α-dimethyl-4-androsten-3-one diacetate is dissolved under nitrogen in a sodium methoxide methanol solution at 0° C. and stirred at room temperature for about 2 hours. The solution is poured onto water and the solid collected by filtration. Recrystallization of the solid from acetonitrile yields the desired 17β,19-dihydroxy-1α,7α-dimethyl-4-androsten-3-one.

EXAMPLE 65

17β,19-Dihydroxy-1α,7α-dimethyl-4-androsten-3-one 17-acetate

To a solution of 17β,19-dihydroxy-1α,7α-dimethyl-4-androsten-3-one diacetate in 10% aqueous methanol is added 1 equivalent of sodium bicarbonate. The solution is heated at its reflux temperature for 1 hour. Methanol is removed under vacuum to half volume and the concentrate is poured onto water. The solid which forms is filtered, air dried and crystallized from hexane to yield 17β,19-dihydroxy-1α,7α-dimethyl-4-androsten-3-one 17-acetate.

Substituting 17β,19-dihydroxy-1α-methyl-4-androsten-3-one diacetate and 17β,19-dihydroxy-4-methyl-4-androsten-3-one diacetate for the 17β,19-dihydroxy-1α,7α-dimethyl-4-androsten-3-one diacetate above results in the preparation of 17β,19-dihydroxy-1α-methyl-4-androsten-3-one 17-acetate and 17β,19-dihydroxy-4-methyl-4-androsten-3-one 17-acetate.

EXAMPLE 66

The following Example is illustrative of the behavioral activity for the compounds of this invention.

Copulatory behavioral tests are conducted in mature, sexually experienced Sprague-Dawley male rats that were either intact, castrated or castrated-andrenalectomized. Castration and adrenalectomy reduces the effect on behavior associated with endogenous steroids and/or their metabolites. The onset and intensity of behavioral responses related to mounting, intromission and ejaculation are determined both prior to and after an interval of at least 2 weeks post-surgery. Five animals per group are subcutaneously administered 500 micrograms/kg of 19-hydroxytestosterone, testosterone or 0.25 ml/kg of olive oil vehicle for a period of 14 days. Ten minute behavioral observations are made in the presence of a receptive female rat on days 2, 8, 12 and 15 of the treatment period.

As shown in the table below, testosterone treatment in both castrated and adrenalectomized - castrated rats approaches that of pre-operative and intact control levels of behavior by about day 12. In contrast thereto castrated - adrenalectomized rats treated with 19-hydroxytestosterone had increases in behavioral parameters approximately 24 hours after initial therapy. Furthermore, these animals remain at this elevated level throughout the entire treatment period. In castrated rats similar but less permanent effects are observed with the administration of testosterone and 19-hydroxytestosterone.

MEAN NUMBER OF INTROMISSIONS AND PERCENT RESPONSE PER 10 MINUTE OBSERVATION PERIOD

| | Pre-Treatment | | | | Treatment Period (14 days) | | | | | | | |
|---|---|---|---|---|---|---|---|---|---|---|---|---|
| | Pre Surgery | | Post Surgery | | 2nd Day | | 8th Day | | 12th Day | | 15th Day | |
| Treatment | No. | % | No. | % | No. | % | No. | % | No. | % | No. | % |
| CASTRATED | | | | | | | | | | | | |
| Vehicle (Olive oil) | 9.2 | 100 | 3.0 | 40 | 0.0 | 0 | 2.4 | 40 | 1.4 | 40 | 0.6 | 40 |
| Testosterone 500 μg/kg s.c. | 9.4 | 100 | 1.0 | 20 | 0.0 | 0 | 0.0 | 0 | 10.8 | 80 | 3.8 | 40 |
| 19-Hydroxytestosterone 500 μg/kg s.c. | 11.2 | 100 | 0.4 | 20 | 0.0 | 0 | 0.0 | 0 | 0.0 | 0 | 8.5 | 50 |
| ADRENALECTOMIZED - CASTRATED | | | | | | | | | | | | |
| Vehicle (Olive oil) | 15.6 | 100 | 7.0 | 80 | 0.0 | 0 | 1.2 | 20 | *NT | | 2.4 | 40 |
| Testosterone 500 μg/kg s.c. | 17.2 | 100 | 4.8 | 60 | 0.0 | 0 | 3.2 | 20 | 9.8 | 100 | 11.0 | 75 |
| 19-Hydroxytestosterone 500 μg/kg s.c. | 19.2 | 100 | 4.8 | 60 | 9.8 | 80 | 12.4 | 80 | 10.2 | 80 | 16.4 | 100 |
| INTACT | | | | | | | | | | | | |
| Vehicle (Olive oil) | 11.8 | 100 | 9.6 | 100 | 13.8 | 100 | 22.8 | 100 | *NT | | 20.8 | 100 |

*NT = Not Tested

EXAMPLE 67

Preparation of a tablet formulation

One thousand tablets for oral use, each containing 25 mg of 19-(1'-ethoxy-1'-cyclohexyloxy)-17-hydroxyandrost-4-en-3-one are prepared according to the following formulation:

| | | Gm |
|---|---|---|
| (a) | 19-(1'-ethoxy-1'-cyclohexyloxy)-17-hydroxyandrost-4-en-3-one | 25 |
| (b) | Dicalcium phosphate | 150 |
| (c) | Methylcellulose, U.S.P. (15 cps) | 6.5 |
| (d) | Talc | 20 |
| (e) | Calcium stearate | 2.5 |

The 19-(1'-ethoxy-1'-cyclohexyloxy)-17-hydroxyandrost-4-en-3-one and dicalcium phosphate are mixed well, granulated with a 7.5% aqueous solution of methylcellulose, passed through a No. 8 screen and carefully dried. The dried granules are passed through a No. 12 screen, blended with talc and calcium stearate and compressed into tablets.

EXAMPLE 68

Preparation of a capsule formulation

One thousand two-piece hard gelatin capsules for oral use each containing 10 mg of 17β,19-di-(2'-tetrahydropyranyloxy)-androst-4-en-3-one are prepared from the following ingredients:

| | | Gm |
|---|---|---|
| (a) | 17β,19-di-(2'-tetrahydropyranyloxy)-androst-4-en-3-one | 10 |
| (b) | Lactose, U.S.P. | 100 |
| (c) | Starch, U.S.P. | 10 |
| (d) | Talc, U.S.P. | 5 |
| (e) | Calcium stearate | 1 |

The finely powdered materials are mixed until uniformly dispersed and filled into hard shelled gelatin capsules of the appropriate size.

In a similar fashion one-piece soft gelatin capsules can be prepared in which the above formulation can be granulated, slugged or compressed directly into a rotary die or plate mold in which the capsule is formed. Alternatively, the above excipients may be omitted and the active ingredient dispensed as a powder directly into the capsule.

EXAMPLE 69

Preparation of an intramuscular injection

A sterile aqueous suspension suitable for intramuscular injection is prepared from the following ingredients:

| | | Gm |
|---|---|---|
| (a) | 17α-ethinyl-17β-hydroxy-19-(1 ethoxy-1'-cyclopentyloxy)androst-4-en-3-one | 1 |
| (b) | Polyethylene glycol 4000, U.S.P. | 3 |
| (c) | Sodium chloride | 0.9 |
| (d) | Polyoxyethylene derivatives of sorbitan monooleate (TWEEN 80) U.S.P. | 0.4 |
| (e) | Sodium metabisulfite | 0.1 |
| (f) | Methylparaben, U.S.P. | 0.18 |
| (g) | Propylparaben, U.S.P. | 0.02 |
| (h) | Water for injection q.s. to 100 ml | |

The parabens, sodium metabisulfite and sodium chloride are dissolved in approximately one-half the volume of water for injection at 80° C. with stirring. The solution is cooled to below 40° C. and the active ingredient is dissolved therein followed by the polyethylene glycol 4,000 and polyoxyethylene derivatives of sorbitan monooleate. The cooled solution is adjusted to the final volume with water for injection and is then sterilized by sterile filtration through a suitable filter. Each one ml of solution contains 10 mg of 17α-ethinyl-17β-hydroxy-19-(1'-ethoxy-1'-cyclopentyloxy)androst-4-en-3-one as the active ingredient.

We claim:

1. A method of enhancing the libido of primates in need thereof which comprises the administration to such primate of a therapeutically effective amount of an androst-4-en-19-ol having the formula

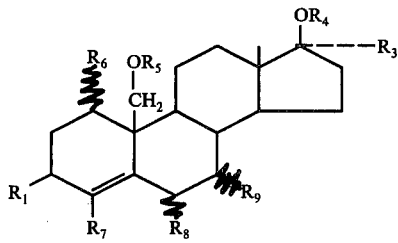

wherein
R$_1$ is selected from the group consisting of H$_2$, oxo and H(OR$_2$),
R$_2$, R$_4$ and R$_5$ are each selected from the group consisting of hydrogen, acyl having from 1 to 12 carbon atoms, lower alkyl having from 1 to 3 carbon atoms, trialkylsilyl in which the alkyl group has from 1 to 5 carbon atoms, triphenylsilyl, 2-tetrahydropyranyl, 4-tetrahydropyranyl, 1-cycloalkenyl having from 5 to 7 carbon atoms, 1-methoxycycloalkyl and 1-ethoxycycloalkyl in which the cycloalkyl group has from 5 to 7 carbon atoms,
R$_3$ is selected from the group consisting of hydrogen, lower alkyl having from 1 to 6 carbon atoms, lower alkenyl having from 2 to 6 carbon atoms, and lower alkynyl having from 2 to 6 carbon atoms, and R$_3$ and
OR$_4$ when taken together is oxo, R$_6$, R$_7$, R$_8$ and R$_9$ are hydrogen and methyl.

2. The method of improving psychic attitudes associated with a decreased libido of primates in need thereof which comprises the administration of a therapeutically effective amount of an androst-4-en-19-ol of claim 1.

3. A method according to claim 1 in which the primates are human.

4. A method according to claim 2 in which the primates are human.

5. A method according to claim 3 in which the androst-4-en-19-ol is administered in a total daily dose of from 0.1 milligram to 3 grams.

* * * * *